(12) United States Patent
Weaver et al.

(10) Patent No.: US 7,994,786 B2
(45) Date of Patent: Aug. 9, 2011

(54) SYSTEM AND METHOD FOR USE OF NANOPARTICLES IN IMAGING AND TEMPERATURE MEASUREMENT

(75) Inventors: John B. Weaver, Hanover, NH (US); Ian Baker, Etna, NH (US); Eric W. Hansen, Lebanon, NH (US)

(73) Assignee: Mary Hitchcock Memorial Hospital, Lebanon, NH (US)

( * ) Notice: Subject to any disclaimer, the term of this patent is extended or adjusted under 35 U.S.C. 154(b) by 287 days.

(21) Appl. No.: 12/141,844

(22) Filed: Jun. 18, 2008

(65) Prior Publication Data
US 2009/0115415 A1 May 7, 2009

Related U.S. Application Data

(60) Provisional application No. 60/944,901, filed on Jun. 19, 2007, provisional application No. 60/974,105, filed on Sep. 21, 2007.

(51) Int. Cl.
*G01V 3/00* (2006.01)
(52) U.S. Cl. ........................................ 324/318; 324/309
(58) Field of Classification Search .......... 324/300–322; 600/407–445; 244/248, 249, 251, 254, 257, 244/258, 260; 250/309
See application file for complete search history.

(56) References Cited

U.S. PATENT DOCUMENTS

| | | | | |
|---|---|---|---|---|
| 5,714,536 | A * | 2/1998 | Ziolo et al. | 524/430 |
| 7,116,102 | B2 * | 10/2006 | Clarke et al. | 324/300 |
| 7,173,130 | B2 * | 2/2007 | Tsien et al. | 544/296 |
| 7,521,928 | B2 * | 4/2009 | Romalis et al. | 324/304 |
| 7,564,245 | B2 * | 7/2009 | Lee | 324/321 |
| 7,576,538 | B2 * | 8/2009 | Meersmann et al. | 324/309 |
| 2003/0085703 | A1 | 5/2003 | Gleich | |
| 2003/0092029 | A1 * | 5/2003 | Josephson et al. | 435/6 |
| 2006/0269612 | A1 * | 11/2006 | Xiang et al. | 424/489 |

(Continued)

OTHER PUBLICATIONS

Weaver, et al, "Frequency Distribution of the Nanoparicle Magnetization in the Presence of a Static as Well as a Harmonic Magnetic Field", May 2008, pp. 1988-1994, vol. 35, No. 5, Publisher: Medical Physics, Published in: US.

(Continued)

*Primary Examiner* — Brij B Shrivastav
(74) *Attorney, Agent, or Firm* — William A. Loginov, Esq.; Loginov & Associates, PLLC

(57) ABSTRACT

This invention provides a system and method that improves the sensitivity and localization capabilities of Magnetic Particle Imaging (MPI) by using combinations of time-varying and static magnetic fields. Combinations of magnetic fields can be used to distribute the signals coming from the magnetic particles among the harmonics and other frequencies in specific ways to improve sensitivity and to provide localization information to speed up or improve the signal-to-noise ratio (SNR) of imaging and/or eliminate the need for saturation fields currently used in MPI. In various embodiments, coils can be provided to extend the sub-saturation region in which nanoparticles reside; to provide a static field offset to bring nanoparticles nearer to saturation; to introduce even and odd harmonics that can be observed; and/or to introduce combinations of frequencies for more-defined observation of signals from nanoparticles. Further embodiments provide for reading of the signal produced by cyclically saturated magnetic nanoparticles in a sample so as to provide a measurement of the temperature of those nanoparticles. The spectral distribution of the signal generated provides estimates of the temperature of the nanoparticles. Related factors may also be estimated—binding energies of the nanoparticles, phase changes, bound fraction of the particles or stiffness of the materials in which the nanoparticles are imbedded.

13 Claims, 13 Drawing Sheets

U.S. PATENT DOCUMENTS

| | | | |
|---|---|---|---|
| 2008/0125312 A1* | 5/2008 | Harutyunyan | 502/232 |
| 2009/0029392 A1* | 1/2009 | Josephson et al. | 435/7.8 |
| 2009/0269284 A1* | 10/2009 | Schultz Sikma et al. | 424/9.34 |
| 2010/0066363 A1* | 3/2010 | Brazdeikis et al. | 324/309 |

OTHER PUBLICATIONS

Weaver, et al, "Imaging Magnetic Nanoparticles Using the Signal's Frequency Spectrum", Mar. 12, 2008, p. 8, vol. 6916, No. 35, Publisher: Dartmouth Hitchcock Medical Center Department of Radiology, Published in: Lebanon, NH.

Dahnke et al, "Limits of Detection of SPIO at 3.0T Using T2 Relaxometry", Jun. 17, 2004, pp. 1-14, vol. 6916, Publisher: Philips Research Laboratories, Technical Systems, Published in: Hamburg, Germany.

Kaiser, et al, "Magnetic Properties of Stable Dispersions of Subdomain Magnetite Particles", Mar. 1970, p. 9, vol. 41, No. 1-13, Publisher: Journal of Applied Physics, Published in: Lowell, MA.

Day, Charles, "Novel Medical Imaging Method Shows Promise", Sep. 2005, pp. 21-22, Publisher: Physics Today, Published in: US.

Gleich, et al, "Tomographic Imaging Using the Nonlinear Response of Magnetic Particles", Jun. 2005, pp. 1214-1217, vol. 435, No. 30, Publisher: Nature Publishing Group, Published in: Hamburg, Germany.

* cited by examiner

US 7,994,786 B2

SYSTEM AND METHOD FOR USE OF NANOPARTICLES IN IMAGING AND TEMPERATURE MEASUREMENT

RELATED APPLICATIONS

This application claims the benefit of U.S. Provisional Application Ser. No. 60/944,901, filed Jun. 19, 2007, entitled SYSTEM AND METHOD FOR IMPROVED NANOPARTICLE LOCALIZATION AND IMAGING, the entire disclosure of which is herein incorporated by reference and U.S. Provisional Application Ser. No. 60/974,105, filed Sep. 21, 2007, entitled SYSTEM AND METHOD FOR MEASURING TEMPERATURE USING THE SPECTRAL DISTRIBUTION OF MAGNETIC PARTICLE IMAGING SIGNALS, the entire disclosure of which is herein incorporated by reference.

FIELD OF THE INVENTION

This invention relates to non-invasive imaging of magnetic particles, and more particularly to Magnetic Particle Imaging (MPI), and to using magnetic particles as biomarkers for measuring particle temperature and binding characteristics of infused magnetic particles.

BACKGROUND OF THE INVENTION

The localization and imaging of magnetic particles and particularly nanoparticles (e.g. discrete particulate structures sized in the nanometer range) is becoming increasingly important for developing new diagnostic methods. Magnetic particles (e.g. iron oxide or iron particles having a magnetic characteristic) have recently been employed in several forms of imaging including MRI (See: H. Dahnke and T. Schaeffter: *Limits of Detection of SPIO at 3.0 T Using T2 Relaxometry, Magnetic Resonance in Medicine* 53:1202-1206 (2005). Recently, a relatively new method termed "Magnetic Particle Imaging" or MPI. MPI was introduced in a paper by B. Gleich and J. Weizenecker entitled *Tomographic Imaging Using the Nonlinear Response of Magnetic Particles, Nature* Vol. 435 (30): 1214-9 Jun. 2005. Currently, this new technique (MPI) has received a good deal of attention in the wider press because of the promise of the method. See: C. Day, *Novel Medical Imaging Method Shows Promise, Physics Today*, Sep. 21-22, 2005. The teachings of each of the above three articles/papers being expressly incorporated herein by reference.

Thus, magnetic particles are becoming important in a wide variety of endeavors and applications. In medical applications, such magnetic particles are being used to identify pathology as well as to treat pathology like cancer and heart disease. In general, magnetic substances are relatively easy to detect using various detection and imaging technologies. A further discussion of the use of MPI, in the imaging of human bodily structures is disclosed in published U.S. Patent Application No. 2003/0085703, entitled METHOD OF DETERMINING THE SPATIAL DISTRIBUTION OF MAGNETIC PARTICLES by Bernhard Gleich, the teachings of which are expressly incorporated herein by reference. Reference will now be made to FIGS. 1 and 2, which illustrate a basic implementation of an MPI system in accordance with Gleich.

The MPI system detects particles in the field-free point 210 (FIG. 2 below) where there is very little static field. Those particles in the field free point produce signal at the harmonics, most strongly at the third harmonic.

As shown in FIG. 1, a plurality 100a, 100b of coil pairs are arranged above (100a) and beneath (100b) a patient (or other subject to be examined) 110 positioned on a table top, which is substantially non-magnetic. As described further below, the patient has been infused with magnetic nanoparticles. These particles can be formed with a variety of substances and in a range of sizes. In one example, the particles each comprise a spherical substrate, for example, of glass which is covered with a soft magnetic layer having a thickness of, for example, approximately 5 nm. This layer can consist, for example, of an iron nickel alloy (for example, permalloy). This soft magnetic layer may be covered, for example, with a further covering layer, which protects the particle against acids and other bodily fluids and/or environmental agents.

The range of these coil pairs defines the examination zone. The first coil pair includes the two identically constructed windings 102a and 102b, which are arranged coaxially above and beneath the patient or sample and conduct equally large but oppositely directed sinusoidal currents (indicated by oppositely arranged X's and dots). The gradient magnetic field thus generated can be represented by the field lines 200 shown in FIG. 2. In the direction of the (perpendicular) axis of the coil pair it has a substantially constant gradient and in a point 202 on this axis (dashed line 210) it reaches the value zero. Starting from this field-free point, the strength of the magnetic field increases in all three spatial directions as a function of the distance from this point. In a zone 210 which is denoted by a dashed circle (the first sub-zone) around the field-free point the field strength is so low that the magnetization of magnetic particles present therein is not saturated, whereas the magnetization is in a state of saturation outside the zone 210. In the zone remaining outside the zone 210 (the second sub-zone 220) the magnetization of the particles is in the saturated state.

The strength of the magnetic field required for the saturation of the magnetization of particles is dependent on their diameter and composition. Smaller particle require a larger magnetic field to saturate them than larger particles. When a coating of a material having a lower saturation magnetization is chosen, lower field values are enabled. The size of the zone 301 determines the spatial resolution of the system, and is partly dependent on the strength of the gradient of the gradient magnetic field and also on the strength of the magnetic field required for saturation. By way of example, for a 100-micron diameter and a gradient of 0.2 T/m of the magnetic field, the zone 210 (in which the magnetization of the particles is not saturated) defines a size of approximately 1 mm.

In order to appropriately image structures within the patient or other subject 100 under examination, the system must extract information concerning the spatial concentration of the magnetic particles within the subject 100. As such, a plurality of coil winding pairs is arranged above and beneath the subject 100 and/or the table top 112.

When a further magnetic field is superimposed on the gradient magnetic field in the examination zone, the zone 210 is shifted in the direction of this additional magnetic field, the extent of the shift being greater as the strength of the magnetic field is greater. When the superimposed magnetic field is variable in time, the position of the zone 210 changes accordingly in time and in space.

In order to generate such temporally variable magnetic fields for any arbitrary direction in space, three further coil winding pairs 104a and 104b, 106a and 106b, and 108a and 108b are provided coaxially with the first winding pair 102a, 102b. The coil winding pair 104a, 104b generates a magnetic field which extends in the direction of the coil axis (dashed line 130) of the coil winding pair 102a, 102b (aligned vertically in this example). To this end, the two windings 104a, 104b are supplied with equal currents which also flow in the same direction as adjacent windings 102a, 102b. The effect of coil winding pair 104a, 104b can also be achieved by superimposing currents flowing in the same direction on the oppositely directed equal currents in the coil winding pair 102a, 102b so that the current in one coil pair decreases while it increases in the other coil winding pair. However, it may be advantageous when the temporally constant gradient magnetic field and the temporally variable vertical magnetic field are generated by separate coil pairs.

In order to generate magnetic fields which extend horizontally in space in the longitudinal direction of the patient/subject 100, and also in a direction perpendicular thereto (e.g. generally parallel to the axis 130), there are provided two further coaxial coil winding pairs 106a and 106b, and 108a and 108b. In this example the coil winding pairs 106a, 106b and 108a, 108b are not of a Helmholz-type—while the coil winding pairs 102a, 102b and 104a, 104b can be of a Helmholz-type. To employ Helmholz-type coil winding pairs to generate horizontal fields would require them to be arranged along the sides of the examination zone—for example, windings each respectively arranged to the left and to the right of the examination zone and in front of and behind the examination zone. This arrangement may be impractical, as it impeded access to the examination area.

Thus, as shown, the windings 106a, 106b and 108a, 108b of the coil pairs are arranged coaxially above and beneath the examination zone, and hence they employ a winding configuration different than that of the coil winding pair 104a, 104b. Note that coils of this configuration are known and available in connection with magnetic resonance apparatus with an open magnet (e.g. open MRI) in which an RF coil pair is arranged above and beneath the examination zone so as to generate a horizontal, temporally variable magnetic field.

FIG. 1 also shows a further pickup/sensing coil(s) 150 which provides for the detection of signals generated in the examination zone. In principle any of the field-generating coil winding pairs 102a and 102b, 104a and 104b, 106a and 106b, and/or 108a and 108b can be used for this purpose. However, the use of a separate receiving coil offers advantages. A more attractive signal-to-noise ratio is obtained (notably when a plurality of receiving coils is used) and the sensing coil(s) 150 can be arranged and switched in such a manner that it is decoupled from the other coils.

In operation, the coil winding pairs 104a and 104b, 106a and 106b, and 108a and 108b receive their currents from current amplifiers 170. The variation in time of the currents $I_x$, $I_y$, and $I_z$ which are amplified and produce the desired magnetic fields is imposed by a respective waveform generator 172. The waveform generators are controlled by a system control unit 174, which calculates the variation in time of the currents as required for the relevant examination method and loads this variation into the waveform generators. During the examination these signals are read from the waveform generators 172 and applied to the amplifiers 170, which generate the sinusoidal currents $I_x$, $I_y$, and $I_z$ required for the coil winding pairs 104a and 104b, 106a and 106b, and 108a and 108b on the basis thereof.

Generally, a non-linear relationship exists between the shift of the zone 210 from its position at the center of the gradient coil system 102a, 102b and the current through the gradient coil system. Moreover, all three coils should generate a magnetic field when the zone 210 is to be shifted along a line extending outside the center 202. This is taken into account by the system's control unit 174 while imposing the variation in time of the currents, for example, by employing appropriate lookup tables. The zone 210, therefore, can be shifted along arbitrarily formed paths through the examination zone.

The signals S received by the sensing coil(s) 150 are applied to an amplifier 180 via a suitable filter 182. The output signals of the amplifier 180 are digitized by an analog-to-digital converter 184 so as to be applied to an image processing unit 186, which reconstructs the spatial distribution of the particles from the signals and the known position of the zone 210 during the reception of the signals S. An image of the sensed particle distribution can be displayed on an appropriate display monitor 188 (or otherwise rendered into a viewable image).

The signal produced from a harmonic field with an additional static field imposed has been characterized as discussed in *Frequency Distribution of the Nanoparticle Magnetization in the Presence of a Static as Well as a Harmonic Magnetic Field*, Medical Physics 35, 1988-1994, 2008, by J. B. Weaver, A. M. Rauwerdink, C. R. Sullivan, I. Baker. The second harmonic produced when there is a static field is larger than the third harmonic providing superior signal to noise. In addition, the size of the static field contributes localization information that contributes to the signal localization. See *Imaging Magnetic Nanoparticles Using the Signal's Frequency Spectrum*, Procedures of SPIE on Medical Imaging, Volume 6916, 6916-35, 2008, by J. B. Weaver, A. M. Rauwerdink, B. S. Trembly, C. R. Sullivan. Further, a combination of harmonic fields produce signal at many specific frequencies which can also be used to contribute localization information.

In medical applications, the ability to attach a nanoparticle to molecular agents that localize in pathology is very promising for both diagnosis and treatment. Also, a highly significant aspect of MPI is the promised sensitivity. Antibody-tagged nanoparticles can be targeted to cancer or other cells in very specific ways but highly selective targeting will generally collect relatively few nanoparticles to a specific location so sensitivity is critical. For example, targeting individual cells would be important to track a metastasis. In view of these promising new medical applications and techniques, it is, thus, highly desirable to refine the above-described system and method for performing MPI to achieve even higher imaging resolution and particle localization accuracy.

SUMMARY OF THE INVENTION

This invention overcomes the disadvantages of the prior art by providing a system and method that improves the sensitivity and localization capabilities of Magnetic Particle Imaging (MPI) by using combinations of static and oscillating magnetic fields. Combinations of magnetic fields can be used to distribute the signals coming from the magnetic particles among the harmonics in specific ways to improve sensitivity and to provide localization information to speed up or improve the signal-to-noise ratio (SNR) of imaging and/or eliminate the need for saturation fields currently used in MPI. In one embodiment, the signal from particles along a static or slowly varying magnetic field are collected rather than collecting signal only from the field free point, in contrast to the prior art, improving the signal and allowing smaller gradients or better signal-to-noise ratio (SNR) to be achieved. In another embodiment, the second harmonic signal from nanoparticles can be enabled by a localized static field scanned across the object rather than saturating the third harmonic to achieve localization as in prior art. In another embodiment, the static field of an MRI system can be used to create a field offset allowing the signal in the second harmonic to be detected, rather than using only the signal at the third harmonic, to create a combined imaging modality where the particles are imaged using magnetic particle imaging and the anatomy is imaged using conventional magnetic resonance imagery (MRI). In another embodiment, a combination of harmonic fields can be used to place the harmonics at frequencies that are not harmonics of the amplifiers so as to reduce noise and provide extra localization information.

In another embodiment, static field coils can be employed in conjunction with selection and drive coils to provide a static offset to the field-free region so that particles are brought nearer to a saturation level therein. In this manner, greater imaging performance is achieved for a given nanoparticle concentration within a subject. In another embodiment, drive coils can be combined with static field and gradient coils the increase the physical range of the sub-saturation region for nanoparticles. Localization of particles includes observing the distribution of signal among the harmonics generated by the particles in conjunction with the monitoring of the control system that generates waveforms in the magnetic-field coils. In another embodiment, static field and gradient coils can be combined with drive coils in a novel arrangement to increase the range of the sub-saturation region and also to provide various regions with static field offset. Localization of nanoparticles entails observing the distribution of signal among the harmonics and incrementing the static field offset and gradient fields while monitoring this function within the imaging system. In yet another embodiment, the static and field gradient coils are combined with multiple drive coils that each transmit at a discrete frequency or frequencies. In this arrangement, localization of the nanoparticles entails observing the distribution of signal among the frequencies generated by nanoparticles and also observing the combination of various frequencies. A variety of additional arrangements of coils and types of generated magnetic fields can be employed in further alternate embodiments.

In further illustrative embodiments this invention provides a system and method for reading the signal produced by cyclically saturated magnetic particles in a sample so as to provide a measurement of the temperature of those nanoparticles. The spectral distribution of the signal generated provides estimates of the temperature. More particularly, the second and third harmonics increase monotonically with decreasing temperature of the particles and increases monotonically with increasing amplitude of the magnetic field saturating the particles, termed the driving field. Further, the ratio of the fifth and third harmonics is monotonically in the same fashion, however, the ratio of the fifth and third harmonics is independent of particle concentration. Because the harmonics and their ratios change monotonically, the temperature can be found from the harmonics or their ratio. The harmonics also change with particle size distribution. However, by observing the harmonic signals as the amplitude of the driving field is changed a calibration curve can be obtained from the sample of particles in vivo. Therefore, this method of estimating temperature can be used for any size distribution obtained in vivo or even changing size distributions. Indeed, the size distribution of the particles injected might be very different from the size distribution in any given position in vivo but this should not affect the results because the calibration curve can be obtained in vivo at any time by changing the amplitude of the drive field. Indeed, the changes observed in successive calibration curves can be used to estimate other properties such as size distribution and kinetics. In addition, once the binding energy is known, the bound fraction can be monitored longitudinally. Related factors may also be estimated using the procedure of this embodiment—that is, binding energies of the nanoparticles and phase changes of the materials in which the nanoparticles are imbedded. In one embodiment, the particle output voltage of a plurality of harmonics (for example the third and fifth harmonics or other combinations) are correlated to derive the temperature of the particles in accordance with a Langevin function, which accounts for the independent, isotropic spins induced in the heated particles. In an exemplary implementation, the sample being measured resides in a pickup coil, which is surrounded by a drive coil. A balancing coil or other technique can be used to reduce the effect of the driving frequency on measurements. Image gradient coils can be employed with corresponding imaging electronics to provide temperature-dependent images of the particles within the sample, or other internal structure. However, the illustrative systems and methods for measuring temperature can be used without imaging as well.

In an illustrative embodiment, particles with antibodies targeted for cancer cells are injected in the subject. Following binding, a very large applied magnetic field is used to heat the particles in the cancer. The ratio of the harmonics would be used to monitor heating to make sure therapeutic temperatures are achieved in the cancer. In another embodiment, the distribution of the applied fields is changes using temperature information to achieve better therapy. In another embodiment, the harmonics at a constant temperature are used to measure the binding strength of the antibody targeting agents for diagnostic or other purposes including the suitability of therapy. In another embodiment, the harmonics at a constant temperature are used to estimate the number of antibody targeted particles that are bound and the number that are unbound for diagnostic purposes or to know when to start therapy. In another embodiment, the harmonics are used to estimate when a phase change has occurred in the material in which the articles are located.

All of the above-described embodiments can be employed as discrete systems and methods or combined with MPI methods or the imaging methods described here or other imaging methods to create images of the parameters measured. For example, by combining a plurality of systems and methods temperature maps or temperature images can be obtained instead of determining the average temperature in a single volume.

BRIEF DESCRIPTION OF THE DRAWINGS

The invention description below refers to the accompanying drawings, of which.

DETAILED DESCRIPTION

I. Improved Localization and Imaging

Figure 1:
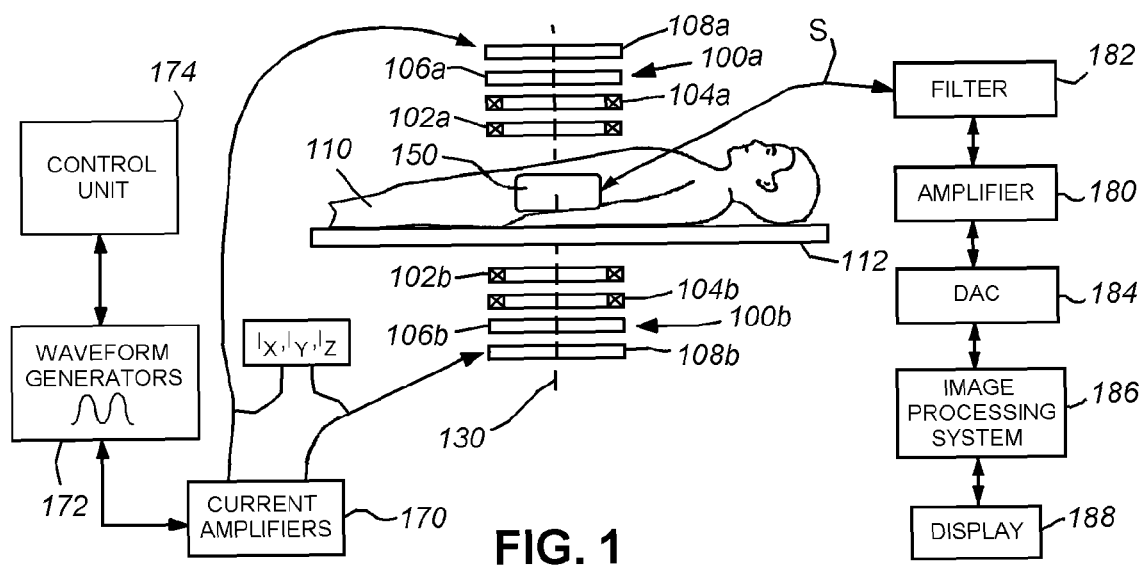
FIG. 1, already described, is a schematic diagram of an exemplary implementation of an MPI system for use in examination of the internal structure of a human patient according to the prior art.
Figure 2:
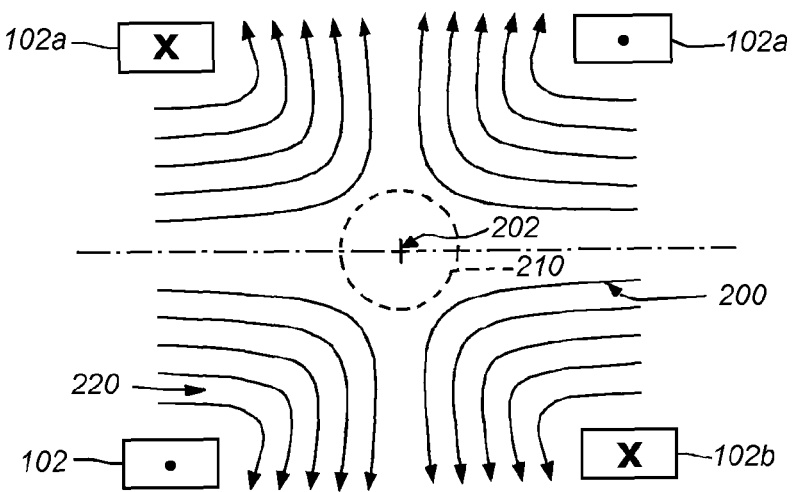
FIG. 2, already described, is a field diagram of the most-adjacent gradient coil to the central field-free zone within the patient/subject.
Figure 3:
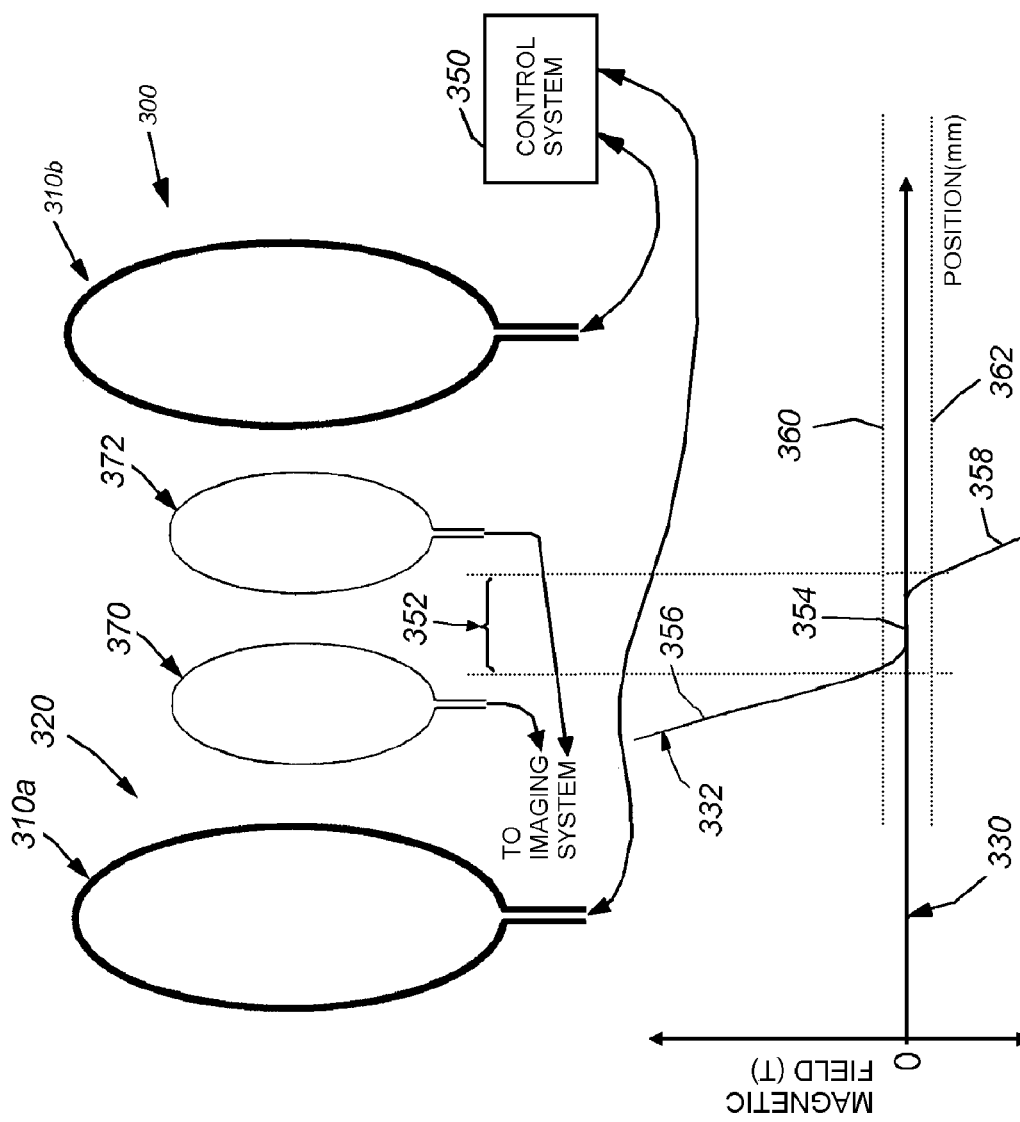
FIG. 3 is highly schematic diagram of the prior art MPI system of FIG. 1 showing the selection and drive coils, sensing coils and detailing the characteristic magnetic field distribution relative to position within the coil arrangement.

Reference is made to FIG. 3 which again describes a simplified MPI system 300 like the MPI system described above with reference to FIG. 1. This system 300 is again discussed and illustrated for the purposes of comparison with the following improved system arrangements described below. The views and graphs depicted are generally two-dimensional, but should be taken to describe the resulting field characteristics in three dimensions. The system 300 consists of groups of drive and selection coils 310a and 310b that define therebetween a magnetic field region 320 that can be characterized by the graph 330. The curve 332 defines the magnetic field across the subject produced by the coils to localize the nanoparticle signal versus position within to the region 320 (e.g. distance from either coil 310a, 310b). As described above, the selection and drive coils are operatively connected with a control system 350. The control system includes appropriate hardware and software (as described above) for amplifying waveforms in the coil windings and generating the desired field-free region 352. This field-free region 352 is exemplified by the flat curve segment 354 which runs approximately along the O-T value of the vertical axis (magnetic field strength). On either side of the field-free region 352, the field increases in opposing directions with the relative proximity to the adjacent coil (curve segments 356 and 358. Beyond the saturating field, exemplified by horizontal limit lines 360 and 362 about the horizontal (position) axis, the field strength is sufficient to saturate all magnetic particles in these positions, thereby eliminating any signal outside the voxel of interest. Particularly, the prior art MPI system 300 of FIG. 3 operates to impose a large, alternating magnetic field on the nanoparticles so that the induced magnetization is saturated. The saturation creates a distortion in the magnetization giving rise to harmonics which can be detected and which allow the number of nanoparticles to be quantified. Nanoparticles that are saturated by a harmonic magnetic field only produce odd harmonics. The system contemplates imaging of the nanoparticles using a static field to saturate all the particles outside the given volume, and as that volume is swept across the subject, an image can then be formed by sensing the harmonics of the swept field using the sensing coils 370, 372 in combination with the above-described imaging system/display.

Hence, the signal from particles along a static or slowly varying magnetic field are collected rather than collecting signal only from the field free point, in contrast to the prior art, thereby improving the signal and allowing smaller gradients or better signal-to-noise ratio (SNR) to be achieved.

Figure 4:
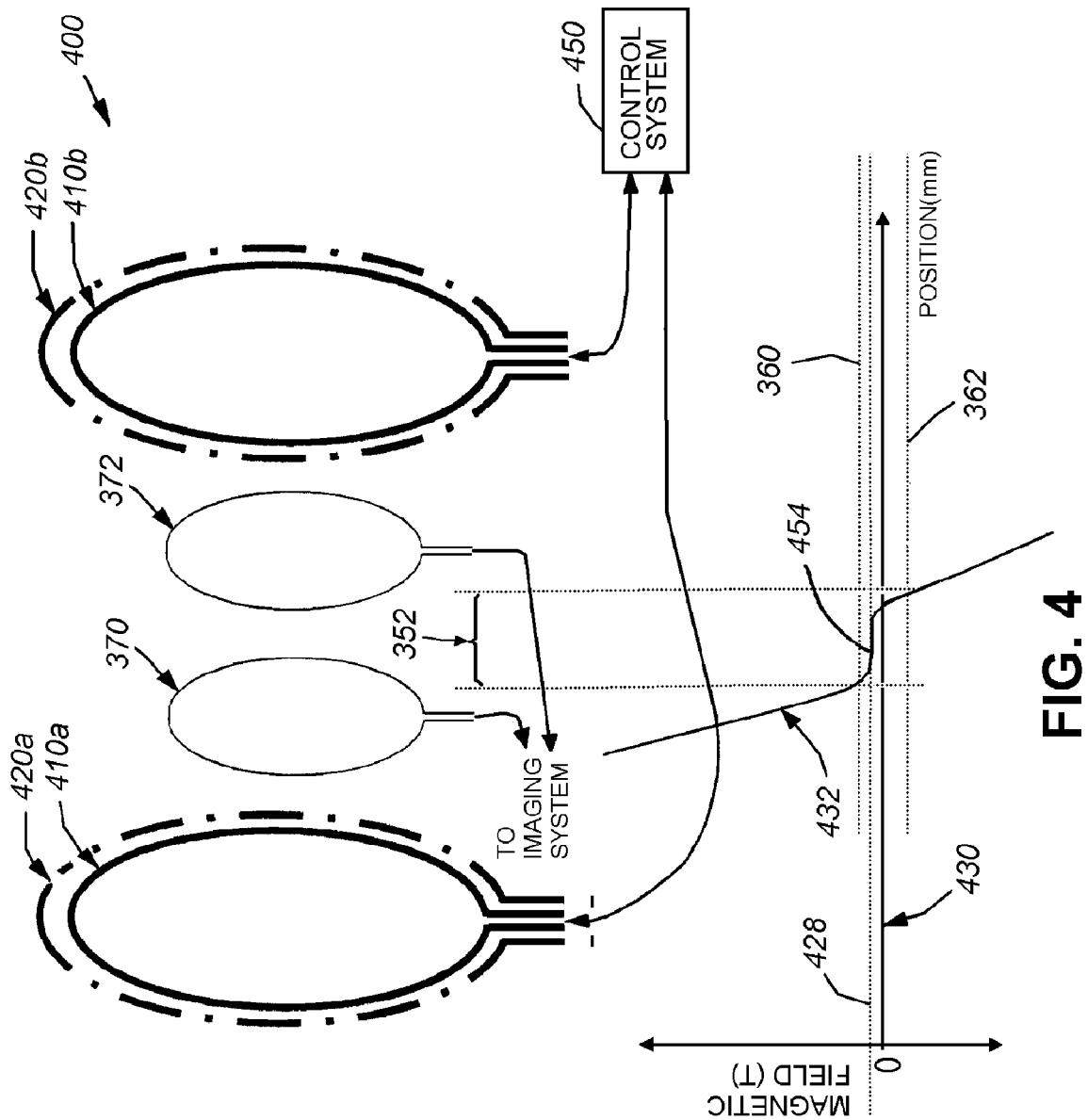
FIG. 4 is a schematic diagram of an improved MPI system and generated magnetic field distribution employing a static field offset according to an embodiment of the invention.

An improved MPI system 400 in accordance with a novel embodiment of this invention is shown in FIG. 4. In this embodiment, the selection and drive coils 410 are essentially the same as the system 300 above. However, they have been supplemented with respective static field coils 420a, 420b that, under direction of the control unit 450 generate a static field offset (horizontal line 428 on the related graph 430). This static field offset moves the horizontal segment 454 of the field strength-versus-position curve 432 away from the O-T value of the vertical axis. In one embodiment, the static field can be generated by MRI coils.

The static field of an MRI system can be used to create a field offset allowing the signal in the second harmonic to be detected, rather than using only the signal at the third harmonic, to create a combined imaging modality where the particles are imaged using magnetic particle imaging and the anatomy is imaged using conventional magnetic resonance imagery (MRI).

Note that a combination of harmonic fields can be used to place the second and third harmonics at frequencies that are not harmonics of the system's sensing amplifiers so as to reduce noise and provide extra localization information.

This static magnetic field nearly saturates the nanoparticles allowing a much smaller alternating magnetic field to thereby saturate the nanoparticles (i.e. the line 428 is moved closer to the upper saturation field 360). High-frequency alternating fields can be used with relatively low power producing relatively high power because the signal is proportional to frequency or alternatively or in addition a swept static field could be employed. Most of the nanoparticles can be saturated many times per unit time, by a sinusoidal current, obtaining both large numbers of nanoparticles saturated and a higher frequency of saturation so the signal is increased both of which increase the signal produced. Note that the use of static field coils can also be employed with others embodiments of the invention as described further below.

Figure 5:
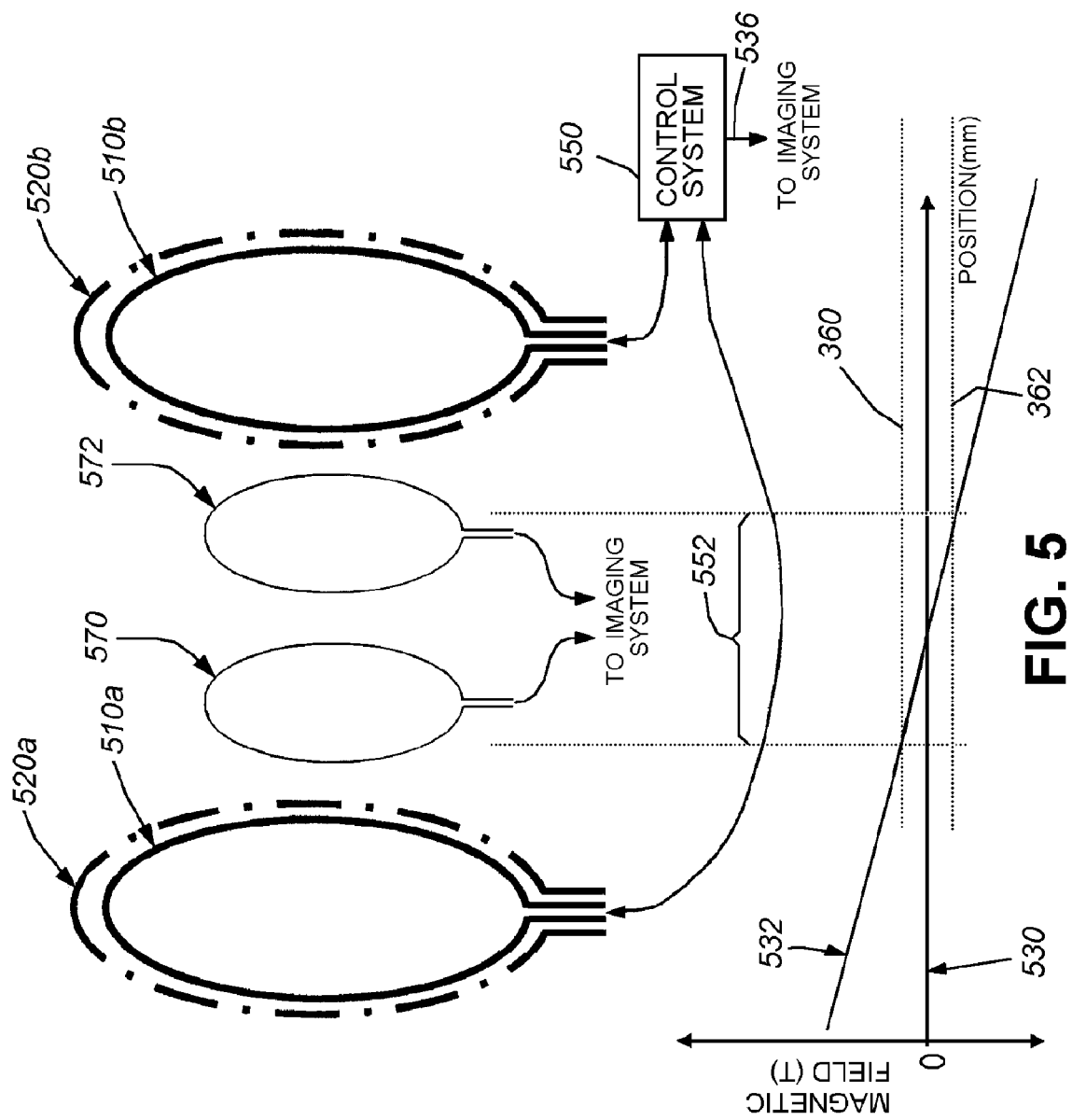
FIG. 5 is a schematic diagram of an improved MPI system and generated magnetic field distribution employing an enlarged region in which a signal is generated according to another embodiment of the invention.

In another embodiment, shown in FIG. 5, the system 500 includes selection and drive coils 510a, 510b similar to those described above as well as static field and gradient coils 520a and 520b, all of which are controlled by a control system 550 that generates appropriate amplitudes and waveforms in the coils. In this embodiment, the static field offset generated by the coils 520*a*, 520*b*, in combination with the gradient serves to enlarge the region 552 from which the nanoparticles generate a signal. Also, it is contemplated that combinations of static and time-varying magnetic fields from the coils can be used to produce harmonics at a variety of frequencies, phases, amplitudes and directions that can be used to localize the nanoparticles or increase the signal generated from the nanoparticles. As such, this implementation adds even (primarily $2^{nd}$) harmonics as well as odd (primarily $3^{rd}$) harmonics, thereby partly increasing the signal. The additional harmonics allows the imaging system (via a link 536) to better localize a signal by observing the distribution of the harmonics along the gradient. In particular, localization entails observing (with the sensing coils 570, 572) the distribution of harmonics and difference signals; e.g., those described in *Microwave Engineering* by Paul Pozar, John Wiley and Sons, pages 503-504, the teachings of which are expressly incorporated herein by reference. The total signal-per-unit time collected increases in this approach because the larger region 552 (see also graph 530 and the flatter curve 532) is employed. In addition, the signal increases because parts of that region are provided with static field offsets that increase the signal from the particles.

Note that a variety of particle-localization techniques can be employed in accordance with various embodiments. For example, multiple-frequency harmonic fields can produce a signal at the difference between the two frequencies and at a variety of other frequencies. When the frequency content changes with position, because one of the alternating field's strengths change with position, the position of the nanoparticles can be isolated by the signal strength at each frequency. Similarly, the phase of the harmonic fields can be used to localize the nanoparticles as well. The uniform and spatially varying magnetic fields can be arbitrary functions of time including, but not limited, to sinusoids, harmonic, square and triangular waves.

Figure 6:
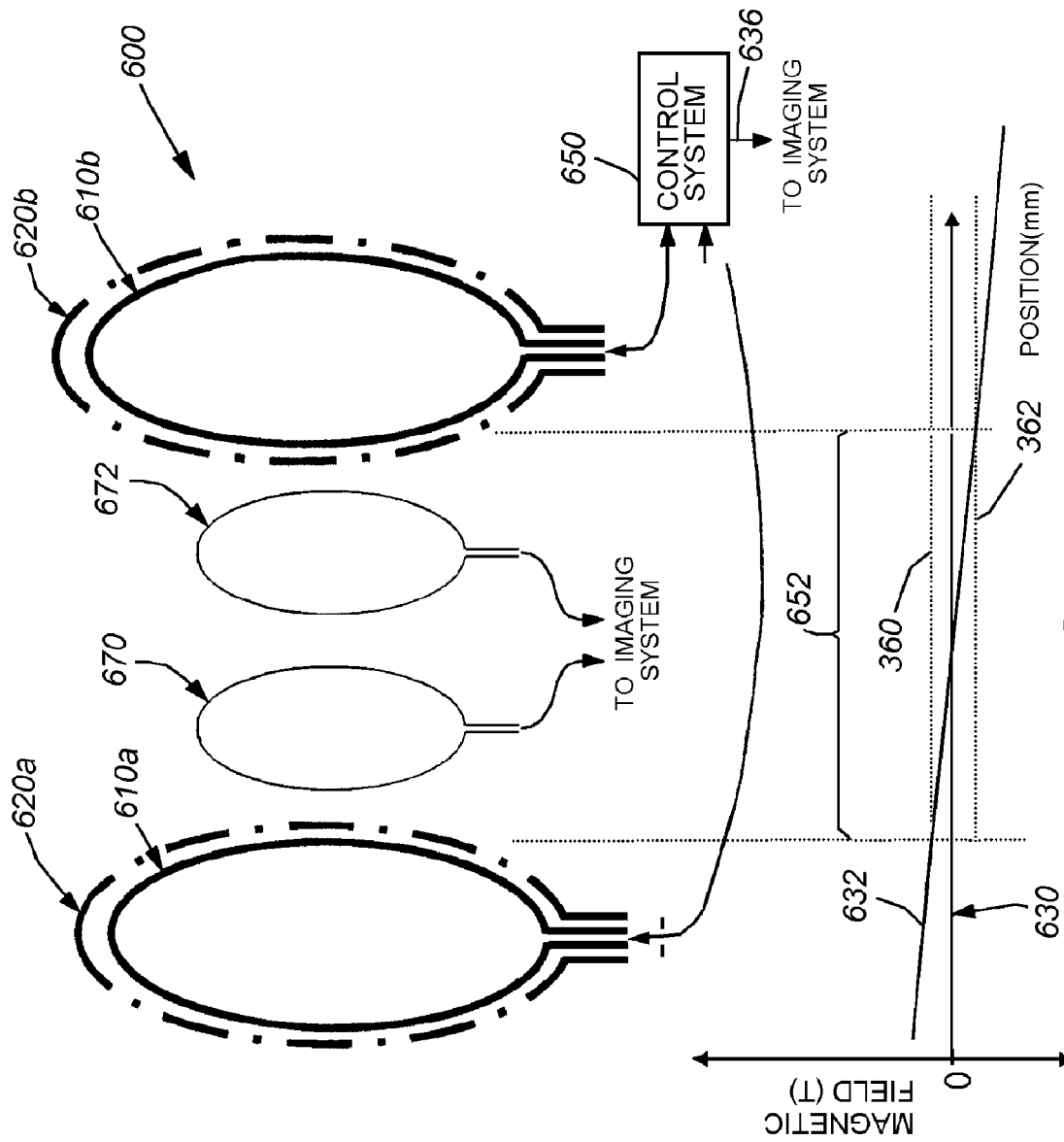
FIG. 6 is a schematic diagram of an improved MPI system and generated magnetic field distribution employing a signal generated from the entire region between drive coils according to yet another embodiment of the invention.

Referring now to FIG. 6, an embodiment of an MPI system 600 is shown, that may be free of the particular coil implementations of, for example, the above-incorporated U.S. Patent Application No. 2003/0085703. The system 600 is generally similar in function to system 500 above, in that it includes drive and selection coils 610*a*, 610*b*, as well as static filed and gradient coils 620*a*, 620*b*. These are controlled to deliver waveforms at a given amplitude to various coils by the control system 650. In this embodiment, the generated nanoparticle signal is generated over substantially the entire region 652 (see also graph 630 and curve 632) between coils 610*a*, 610*b*, 620*a*, 620*b*, because the coils have now been arranged to create sub-saturation-level fields (within graph field-strength limit lines 360, 362) across this entire region 652. This arrangement generates identifiable even and odd harmonics are created in the particle signal in a manner described above with reference to the system 500. The generation can be monitored by the imaging system through a link 636 with the control system 650.

More particularly, in this embodiment, localization of the signal from nanoparticles entails observing (with the sensing coils 670, 672) the distribution of harmonics and difference frequencies, and incrementing (with control system 550) the static field offset and gradient field (via coils 520*a*, 520*b*) to achieve different predetermined values. As such the total signal-per-unit time collected is significantly increased both due to the significantly larger region 652 and because parts of the region have static offsets.

Figure 7:
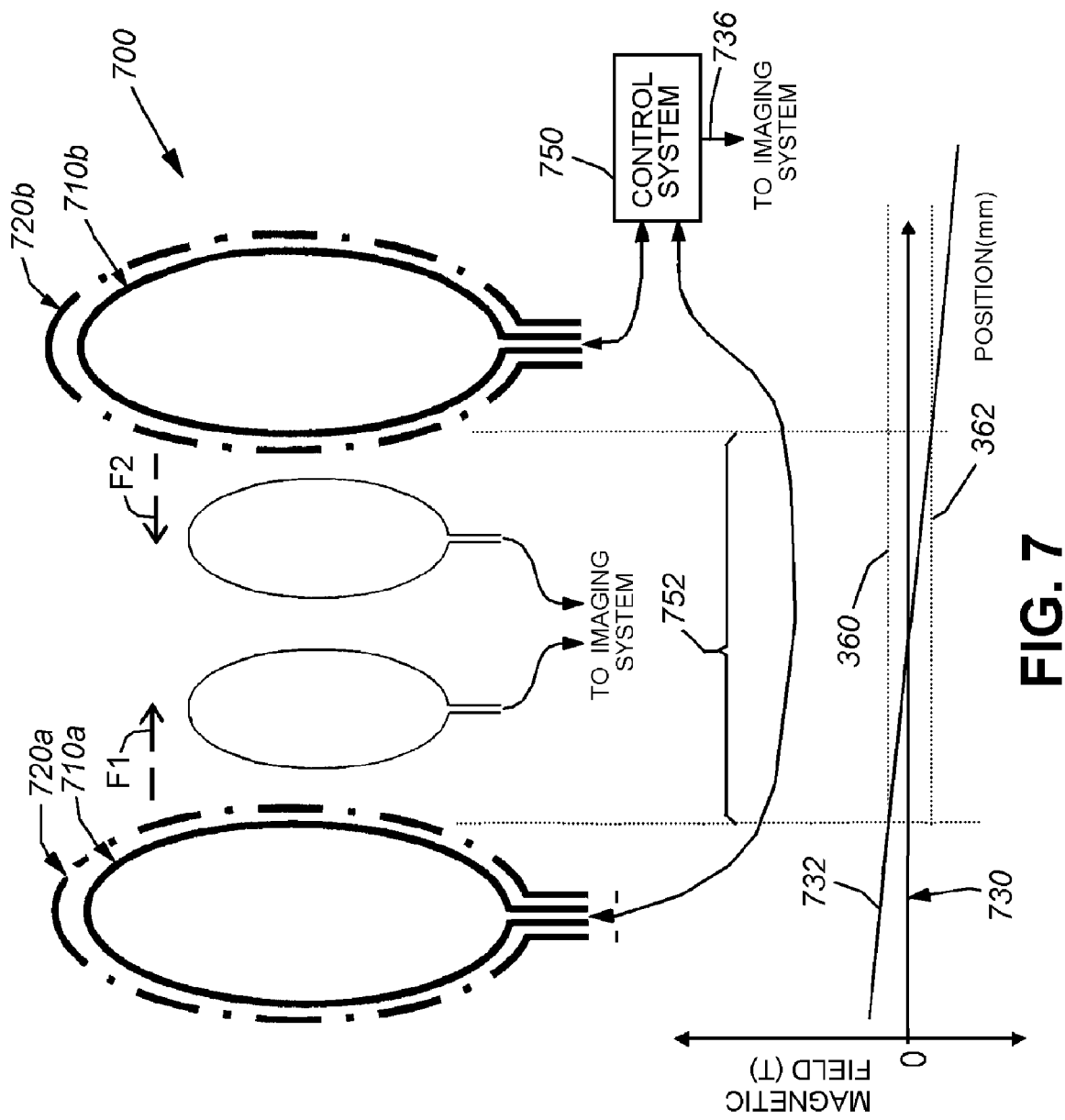
FIG. 7 is a schematic diagram of an improved MPI system and generated magnetic field distribution employing a signal generated from the entire region between drive coils, and the drive coils each generating a different frequency, according to yet another embodiment of the invention.

FIG. 7 details another embodiment of an MPI system 700 in accordance with this invention that may employ arrangements of components similar to those of the system 600 described above. In this embodiment, the signal is also desirably generated across the entire region 752 between coils (as denoted by the graph 730 and curve 732). Notably, in this embodiment, the control system 750 drives each of two drive coils 710*a* and 710*b* at different frequencies (F1 and F2, respectively). Static and gradient coils 720*a*, 720*b*, like those described above, are also employed and function similarly to the systems described above. The two frequencies F1 and F2 generated by the respective drive coils 710*a*, 710*b* result in the generation of signal at a series of interference frequencies that depend on the relative amplitude of the drive fields at the two frequencies. More coils at different frequencies can be added to further localize the nanoparticles.

Localization of the signal from nanoparticles within the subject entails observing the distribution of harmonics and the combinations of frequencies, which is characteristic for each position relative to the drive coils and gradient coils. The characteristic combination of signal strengths for each position allows the position of the nanoparticles to be identified by inverting the measured distribution of signal strengths. This allows for more accurate resolution of particles as the frequencies generated by the coils are correlated via the control system link 736 with the imaging system. In addition, as described above, the larger region and static offset provided by the coil arrangement of this embodiment desirably provides a higher signal strength from nanoparticles.

It should be apparent that a variety of arrangements and combinations of magnetic-field-generating components can be provided to effect imaging in accordance with alternate embodiments of this invention. For example, nanoparticles can be imaged with the subject on a fixed stage that is then moved into an MRI device for imaging of the anatomy. An MPI system in accordance with this invention is mounted in conjunction with the MRI and the subject is infused with a low concentration of nanoparticles. This hybrid or combination system, thus, employs the MRI to image the anatomy and the MPI to image the nanoparticles in the very low concentrations. The same subject-support structure/stage can be used to facilitate co-registration between the two systems. In particular, the acquired images of each system can be co-registered so the nanoparticle image is co-registered with the MRI anatomy in the imaging system. This arrangement can therefore be used as PET-CT systems are employed clinically. The method of increasing the signal from the nanoparticles described above for systems 500 and 600 is achieved if the correct place in the static field is used for magnetic particle imaging.

II. Temperature Sensing

It is recognized that nanoparticles can be heated by remote mechanisms, including electromagnetic excitation (i.e. hysteresis). The heating of magnetic particles, infused into a local region of a patient's body can be used in the important application of hyperthermia treatment. That is a localized region of the body is heated to eliminate thermally sensitive cells and tissues, such as those often encountered in various forms of cancer. By understanding how magnetic particles react under varied temperature, one can also derive information and images of the particles' relative temperature and the temperature distribution within the body or other internal structure. Other characteristics, such as phase change can also be imaged and mapped. More particularly, the signal produced by cyclically saturated magnetic nanoparticles can provide a measurement of the temperature of those nanoparticles. The spectral distribution of the signal generated provides estimates of the temperature. Related factors may also be estimated: binding energies of the nanoparticles and phase changes or stiffness of the materials or cells to which the nanoparticles are connected. Note also that there are many other possible applications for measurement of temperature in addition to those in the field of medical hyperthermia treatment.

Figure 8:
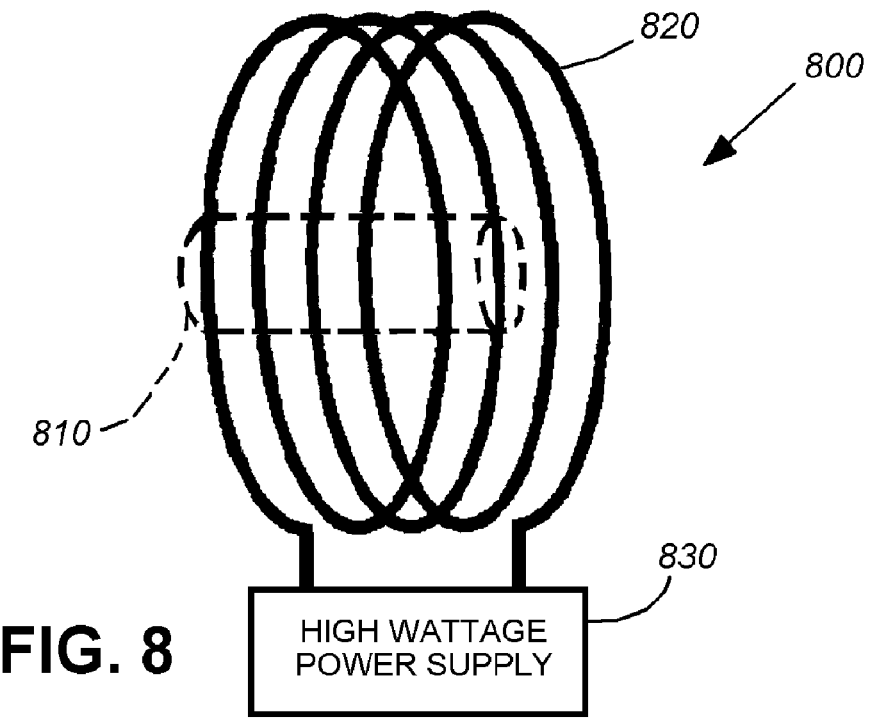
FIG. 8 is a schematic diagram of an alternating current heating coil for activating a sample having magnetic nanoparticles according to this invention.

FIG. 8 is a schematic diagram detailing a generalized arrangement 800 for heating infused magnetic nanoparticles contained in a sample 810 or other internal structure (shown in phantom) according to an embodiment of this invention. The "sample" as shown and described herein can be a simple container with a heatable medium, or a more complex structure, such as the above-described human body. The term "subject" can be used as an alternative to the word "sample". This basic example includes only the heating element (no imaging components), which is a liquid-cooled coil 820 that is interconnected to an alternating current power supply having a sufficient power level and frequency to generate the desired heating effect in the sample 810.

Figure 9:
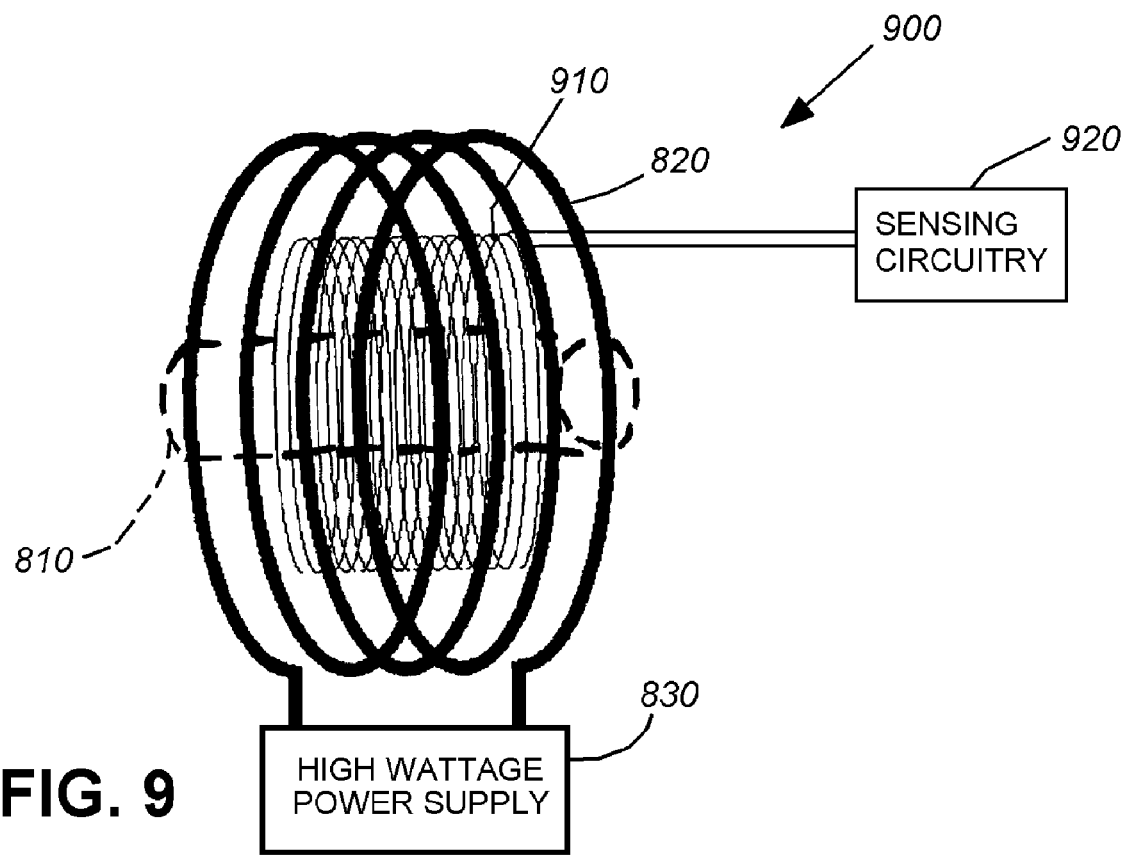
FIG. 9 is a schematic diagram of the alternating current heating coil of FIG. 8 in combination with a coaxial pickup coil that senses output signals in the nanoparticles of the sample in response to excitation by the heating coil according to an illustrative embodiment.

As shown in FIG. 9, the arrangement 900 includes a pickup coil 910 located coaxially between the nanoparticles heating coil 820 and the nanoparticle-containing sample 810. Note that the heating coil 820 is exemplary and a variety of alternate techniques can be employed to heat nanoparticles within an internal structure in alternate embodiments of the invention. This arrangement is a basic embodiment of a temperature-measurement system in which the principles of this invention can be applied to allow interconnected sensing circuitry 920 (operating in accordance with the procedures described below) to measure the temperature of the nanoparticles of the sample 810 at predetermined locations therein.

Figure 10:
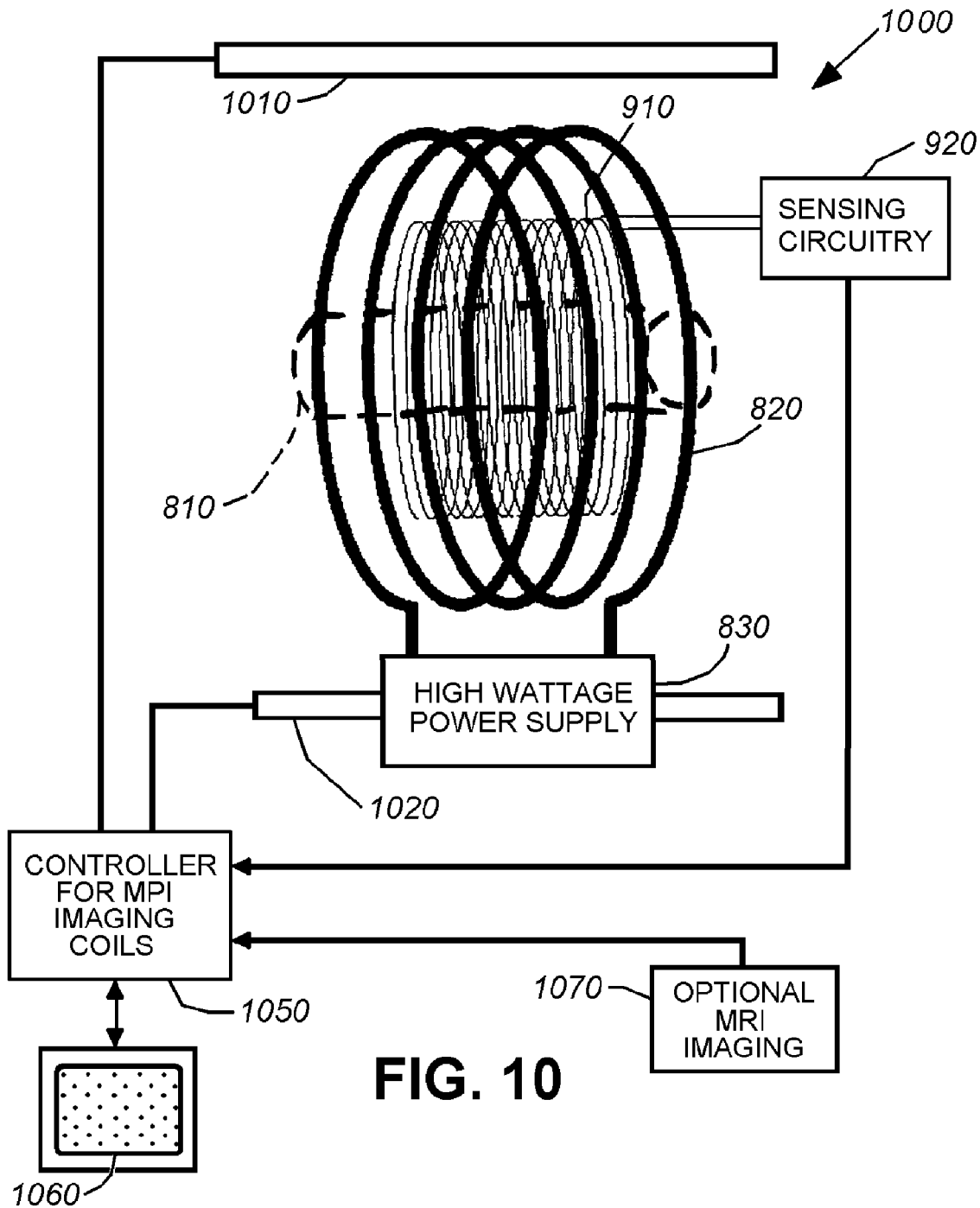
FIG. 10 is a schematic diagram of the alternating current heating coil and pickup coil of FIG. 9, and further including imaging coils and associated imaging electronics for forming an image of the heated nanoparticles within the sample, according to an embodiment of this invention.

Referring now to FIG. 10, an MPI imaging system according to a conventional implementation, or an improved version as contemplated herein, is incorporated into the temperature measurement arrangement 900 of FIG. 9. The resulting arrangement 1000 includes a pair of opposed MPI imaging field coils 1010 and 1020 adapted to generate an image of the excited nanoparticles (which can be also acted upon by other MPI gradient coils (not shown) of conventional or improved design). The image is processed by an appropriate controller 1050, which interacts with the sensing circuitry 920 of the pickup coil 910, as shown. In this manner, the sensed localized temperature and temperature variation can be mapped with respect to an image that can be viewed on an interconnected display 1060.

The measurement of temperature by the controller 1050 and sensing circuitry 920 relies upon a model for the hysteresis curve exhibited by the magnetically excited nanoparticles in the sample 810. This model describes the magnetization of the nanoparticles, which is what produces the underlying signal that is observed by the pickup coil 910. The model used for independent, isotropic spins is a Langevin function. Even in systems where the superparamagnetic model is not strictly applicable, the model provides a good estimate of temperature. The basis for the model is that thermal motion prevents the nanoparticles from aligning perfectly with respect to the applied magnetic field (produced via the coil 820). The result is a balance between the forces induced by the applied magnetic field and thermal activity of the nanoparticles.

Figure 11:
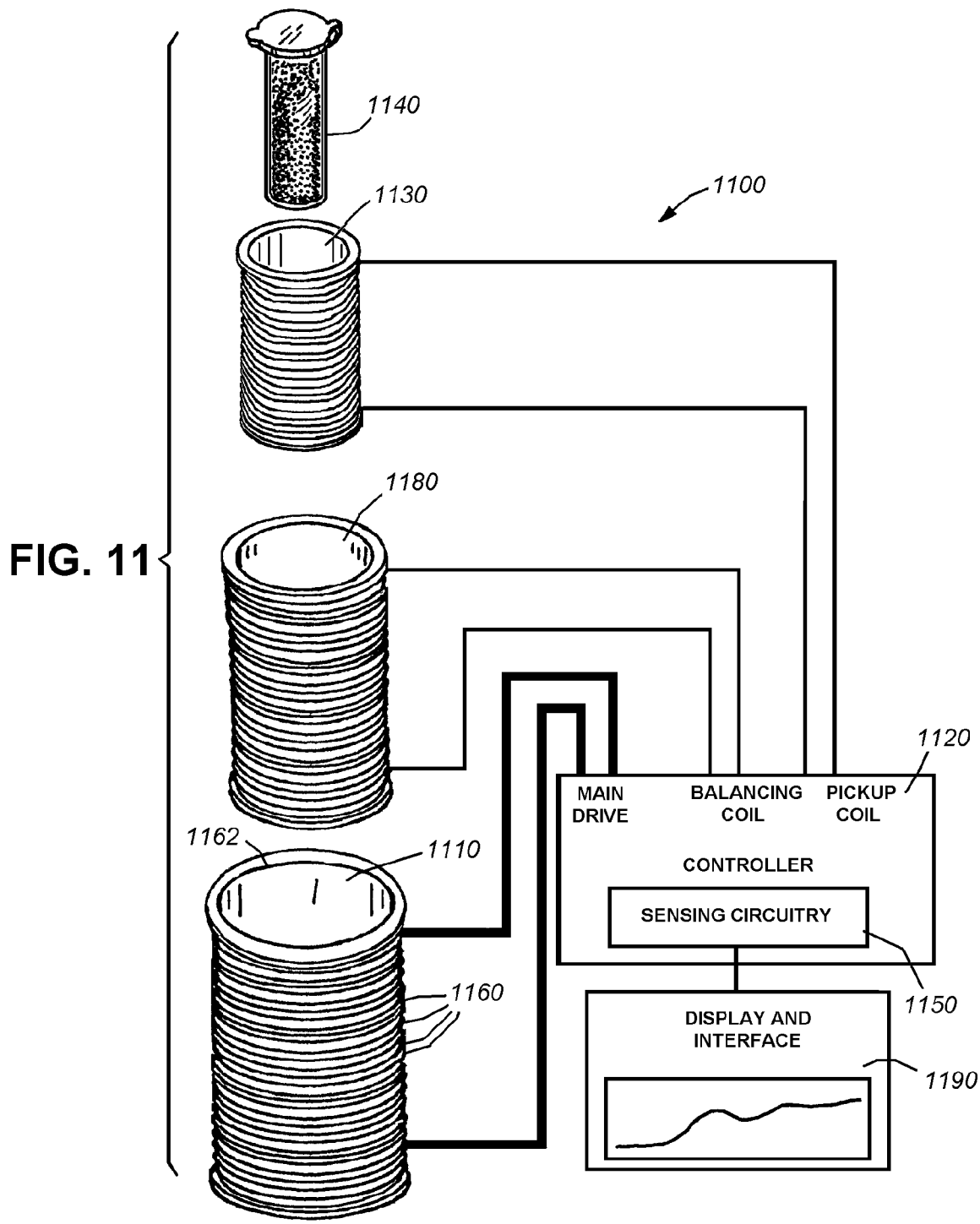
FIG. 11 is an exploded perspective view of an arrangement for sensing the temperature of heated nanoparticles in a sample consisting of a coaxial drive, balancing and pickup coil, and associated sensing/control circuitry according to an illustrative embodiment.
Figure 12:
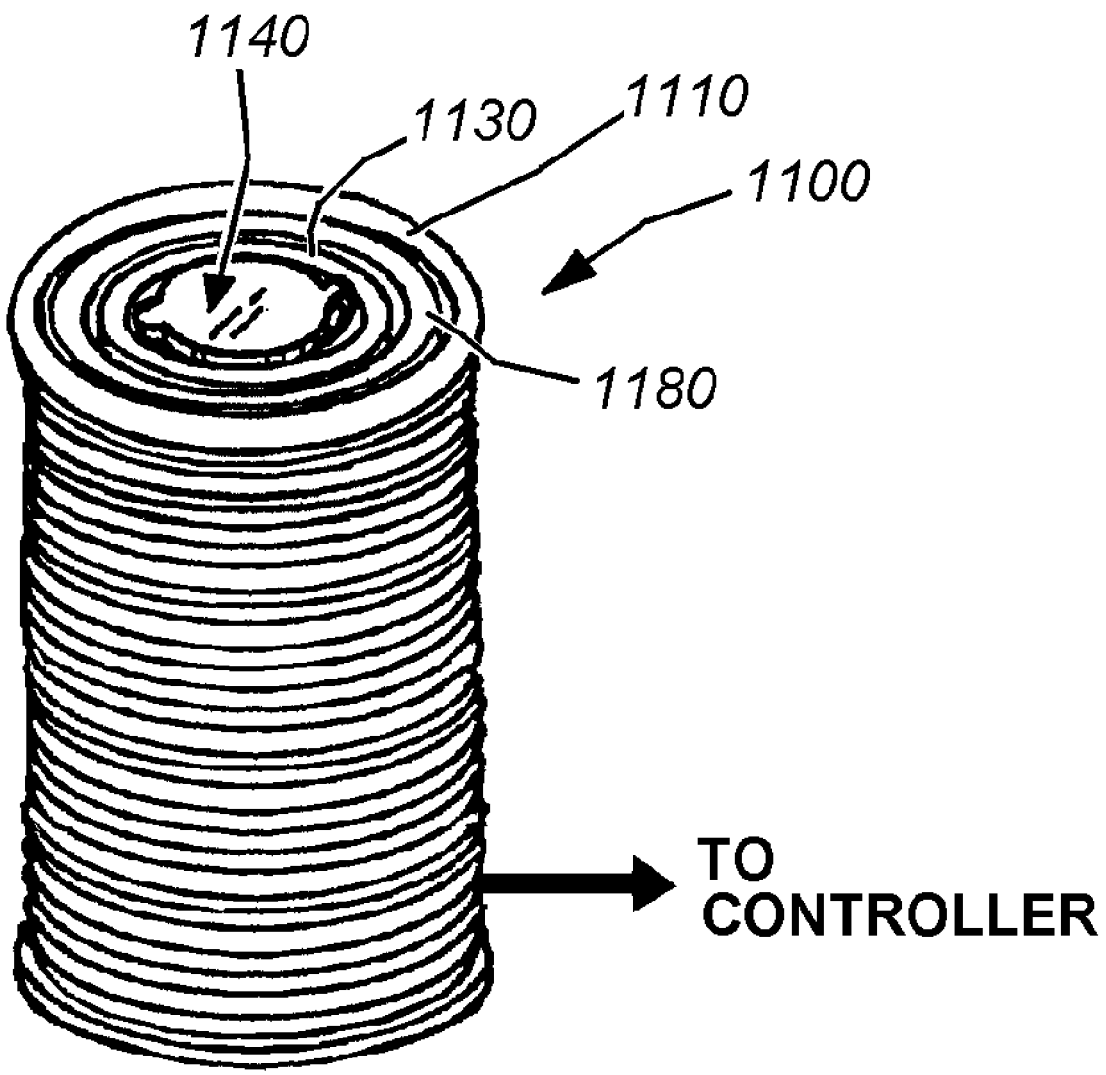
FIG. 12 is a perspective view of the assembled temperature-sensing arrangement of FIG. 11 with the sample inserted thereinto.

An exemplary arrangement 1100 employed to test the temperature-measurement principles described herein (for example, as provided in FIG. 9) is shown in respective exploded and assembled views in FIGS. 11 and 12. This example comprises resonant coil 1110 that drives the magnetization harmonically using an appropriate alternating current drive circuit that is part of a controller 1120. The receive circuit is a pickup coil 1130 that resides coaxially within the drive coil 1110. The pickup coil 1130 records the voltage induced in the particles by the magnetization. In this embodiment, the particles are placed in a magnetically-transparent container 1140 that resides coaxially within the pickup coil 1140. In alternate embodiments other techniques for suspending a sample or sample within the pickup coil 1140 can be employed. The signal voltage at each harmonic frequency is measured by a sensing circuitry 1150 within the controller, which is interconnected to the pickup coil. The drive coil 1110 is characterized as a solenoid resonant coil having (in this example) approximately 1400 wire turns 1160 along a cylinder which is approximately 10 cm long. The sinusoidal current is produced by an audio amplifier fed by a signal generator within the controller circuit 1120. The sinusoidal voltage is set at the resonant frequency of the coil 1110. In this embodiment, the pick up coil 1130 resides coaxially inside both the drive coil 1110 and a series-connected balancing coil 1180 placed at the end of the drive coil 1110 and coaxially between the drive coil and the pickup coil. The balancing coil is optional in alternate embodiments. In this example, the balancing coil 1180 serves to reduce the voltage at the drive frequency so the signals generated by the nanoparticles can be amplified sufficiently to be recorded by the controller 1120. Graphical and/or alphanumeric readings of temperature can be provided by an interconnected display and user interface 1190 of any acceptable type, which is connected to the controller 1120 and sensing circuitry 1150.

In a group of magnetically activated particles, the characteristic hysteresis curve determines the magnetization induced in a material by a time-varying magnetic field. Even for relatively high concentrations of suspended nanoparticles, such as those present in magnetic fluids (ferrofluids for example), the magnetization is well-defined by treating the particles as independent, isotropic spins governed by a combination of statistical thermal fluctuations and the applied magnetic field. See R. Kaiser and G. Miskoloczy, *Magnetic Properties of Stable Dispersions of Subdomain Magnetite Particles*, J. Appl. Phys. 41 (1970) 1064-72, which is incorporated by reference herein as further background information. It follows that suspensions of nanoparticles should be accurately described by the same theory because the particles are more disperse and are small enough to be characterized as a single magnetic domain. The hysteresis curve for a group of identical nanoparticles should be well-described by a Langevin function. See Kaiser. Hence, the magnetization, M, for a harmonic driving field is:

$$M = M_0 \left\{ \cosh\left(\frac{vM_0 H}{4\pi kT}\right) - \left(\frac{vM_0 H}{4\pi kT}\right)^{-1} \right\} \qquad \text{Eq. 1}$$

where M is the magnetization, $M_0$ is the bulk magnetization, v is the volume of the particle, H is the applied field, k is the Boltzmann constant and T is the absolute temperature. In this case, the applied field consists of the sinusoidal field, $H_s = H_0 \sin(\omega t)$, and the constant bias field (generated by bias coils), $H_{bias}$:

$$M = M_0 \left\{ \cosh\left(\frac{vM_0(H_0\sin(\omega t) + H_{bias})}{4\pi kT}\right) - \left(\frac{vM_0(H_0\sin(\omega t) + H_{bias})}{4\pi kT}\right)^{-1} \right\} \qquad \text{Eq. 2}$$

Note that it is useful to think about the effects of temperature as an effective field which scales the applied field:

$$M = M_0 \left\{ \cosh\left(\frac{H_0 \sin(\omega t) + H_{bias}}{H_{TE}}\right) - \left(\frac{H_0 \sin(\omega t) + H_{bias}}{H_{TE}}\right)^{-1} \right\} \quad \text{Eq. 3}$$

where $$H_{TE} = \frac{4\pi k T}{v M_0} \quad \text{Eq. 4}$$

is the temperature equivalent field. The value $H_{TE}$ scales the applied field in the above Eq. 3, so for a large value of $H_{TE}$, a correspondingly larger applied field is required to influence the nanoparticles. $H_{TE}$ is larger for smaller particles, and also for particles with a smaller bulk magnetization or for particles having higher temperatures. The thermal disordering of the nanoparticle magnetizations, reflected by $H_{TE}$, reduces the ability of the applied field to align the individual nanoparticle magnetizations into a macroscopic effect.

It should be noted that collections of sensed particles of different sizes are described by multiple Langevin functions, and although the characteristic properties of the hysteresis curve remain the same, the shape of the curve depends on the distribution of sizes and properties. The size distribution is generally normally distributed. The primary effect of the particle radius is on the corresponding particle volume of the nanoparticle, v, but the particle size also affects the coercive field. The coercive field is a measure of the phase of the magnetization relative to the applied field and does not influence the shape of the hysteresis curve, just the translation of it which can be represented as a time shift in Eq. 3 above. A time shift represents a phase change in the frequency domain so the effect of nanoparticle size on the coercive field causes interference between the magnetizations of the nanoparticles of different sizes.

The most stable technique for estimating $H_{TE}$, and therefore the particle temperature, is by employing a least squares fit of the particle's signal at three or more harmonic frequencies to those calculated by a simple Langevin function. There exists no redundancy between signals, and if a significant signal is observed at all the frequencies, the temperature estimates at each harmonic will be reasonably stable with respect to each other. Hence the calculation of temperature based upon a plurality of harmonics allows for a fairly accurate and reliable estimate of actual particle temperature.

Figure 13:
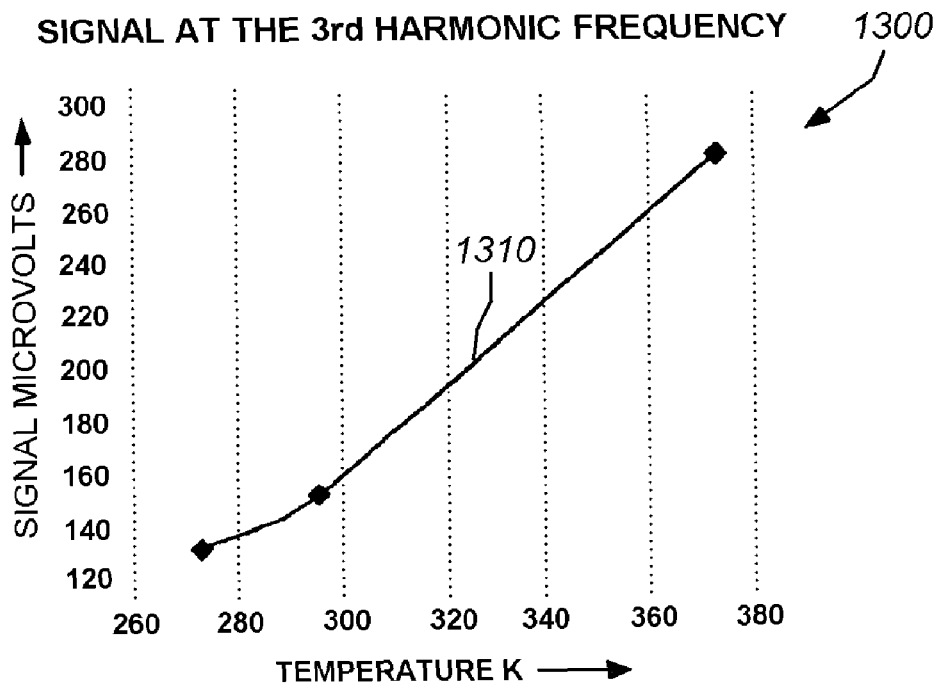
FIG. 13 is a curve of an exemplary output-voltage-to-temperature curve for the third harmonic of the nanoparticle output signal sensed by the pickup coil of the illustrative temperature-sensing arrangement.
Figure 14:
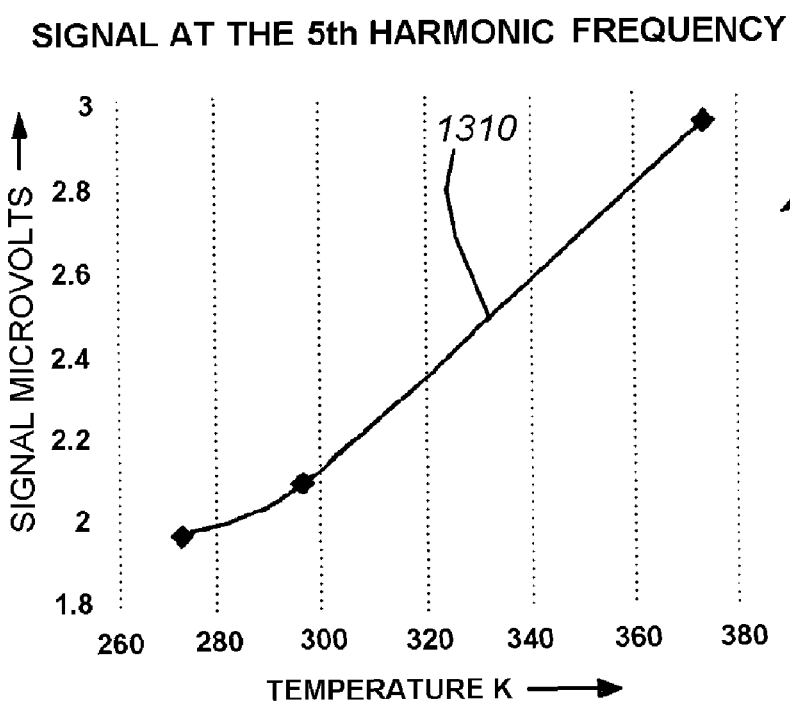
FIG. 14 is a curve of an exemplary output-voltage-to-temperature curve for the fifth harmonic of the nanoparticle output signal sensed by the pickup coil of the illustrative temperature-sensing arrangement.

Referring to the exemplary curves of FIGS. 13 and 14 (1300 and 1400), the respective signal outputs for the third and fifth harmonics in a functional example (refer to FIGS. 11 and 12 above). Each curve 1310 and 1410 respectively plots the measured signal in microvolts versus the absolute temperature (Kelvin) for the measured particles. As shown, the signal at each harmonic frequency increases generally with temperature, thereby providing the requisite technique to measure nanoparticle temperature according to this invention. Note that the curves 1310, 1410 are highly similar in slope and profile and relatively linear at higher temperatures in which the particles will normally be measured. The curve 1310 for the third harmonic is nearly two orders of magnitude greater than the curve 1410 for the fifth harmonic, allowing for separation of the respective signals.

Note that the second and third harmonics increase monotonically with decreasing temperature of the particles and increases monotonically with increasing amplitude of the magnetic field saturating the particles, termed the driving field. Further, the ratio of the fifth and third harmonics is monotonically in the same fashion, however, the ratio of the fifth and third harmonics is independent of particle concentration. Because the harmonics and their ratios change monotonically, the temperature can be found from the harmonics or their ratio. The harmonics also change with particle size distribution. However, by observing the harmonic signals as the amplitude of the driving field is changed a calibration curve can be obtained from the sample of particles in vivo. Therefore, this method of estimating temperature can be used for any size distribution obtained in vivo or even changing size distributions. Indeed, the size distribution of the particles injected might be very different from the size distribution in any given position in vivo but this should not affect the result because the calibration curve can be obtained in vivo at any time by changing the amplitude of the drive field. Indeed, the changes observed in successive calibration curves can be used to estimate other properties such as size distribution and kinetics. In addition, once the binding energy is known, the bound fraction can be monitored longitudinally.

Figure 15:
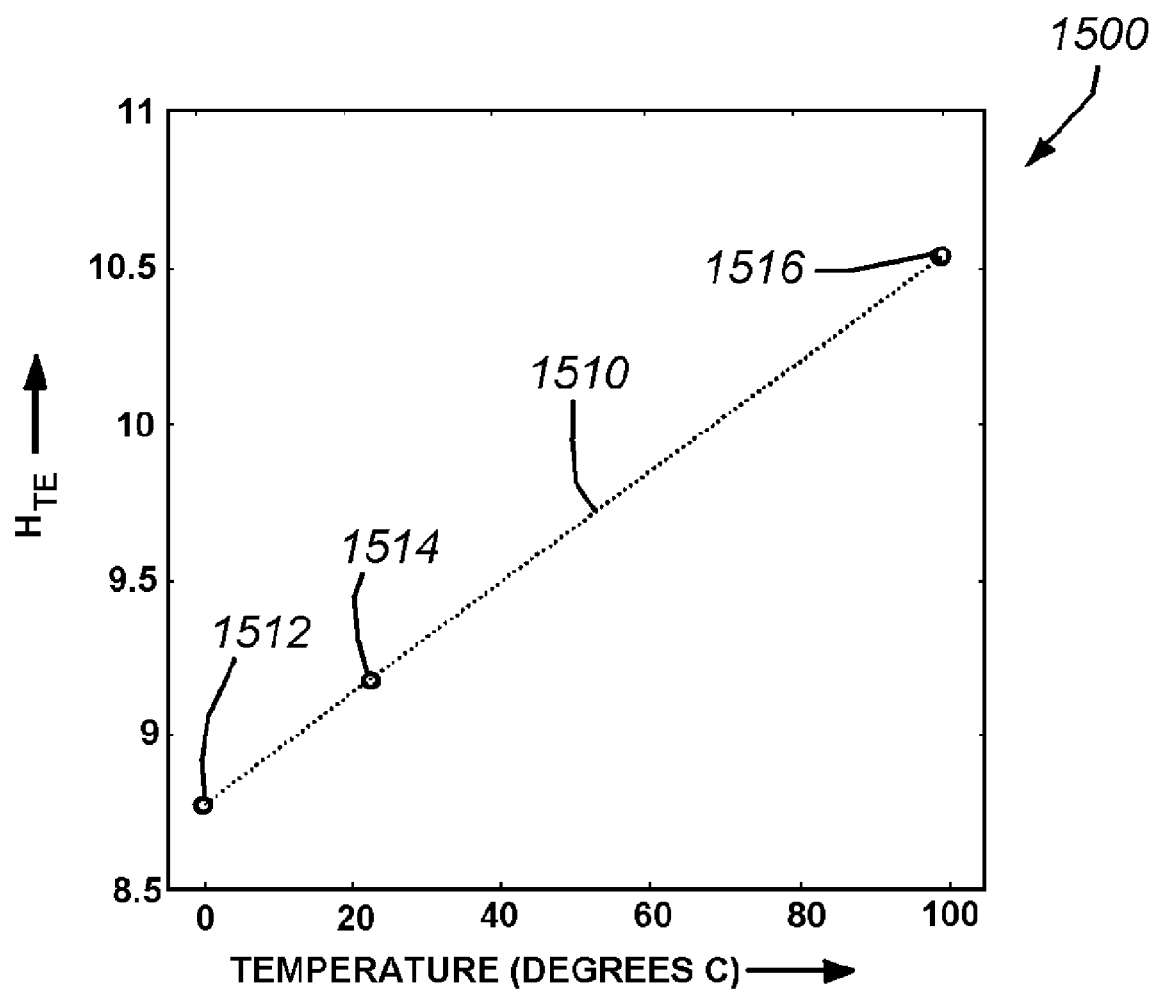
FIG. 15 is an exemplary curve of the relationship between the field value $H_{TE}$ with respect to actual nanoparticle temperature.

An example of a resulting estimate of $H_{TE}$ is shown in FIG. 15, which is a graph 1500 of a curve 1510 which plots measured points 1512, 1514 and 1516 for the measurement $H_{TE}$ versus Temperature (in degrees C.) in the exemplary implementation. As depicted, the $H_{TE}$ estimate as a function of temperature increases linearly with temperature as suggested by Eq. 4. The spectrum at zero-bias field was used to estimate the $H_{TE}$ and the Langevin function modeling $H_{TE}$ is shown. The Langevin function matches the spectra well at low bias fields only showing that the particle output signal is dominated by larger nanoparticles at low bias fields.

Estimates of the ratio $H_o/H_{TE}$ can also be generated from the ratio of the signals at the third and the fifth harmonic frequencies with no bias field and $H_{TE}$ itself can be estimated if $H_o$ is also known and the range of $H_{TE}$ is known. The ratio of the signal at the third and fifth harmonic frequencies is independent of $M_o$ and decreases monotonically between zeros in the fifth harmonic with increasing ratio $H_o/H_{TE}$, so the ratio $H_o/H_{TE}$ can be obtained uniquely from the ratio of the signals between harmonics. $H_{TE}$ includes the effect of nanoparticle volume, v, and the bulk magnetization, $M_o$, which completely characterizes the nanoparticles for MPI if the nanoparticles are of a single size. However, once these parameters are known at one temperature, changes in temperature can be measured by measuring $H_{TE}$, which is directly proportional to temperature. The accuracy of these temperature estimates depends on the size distribution of the nanoparticles.

As noted generally above, a basic application for the foregoing arrangements and procedures is for continuously measuring the temperature of the magnetic nanoparticles used to heat cancer cells in magnetic nanoparticle hyperthermia. A current limitation in the effective use of hyperthermia treatment is it is difficult to ascertain how hot the tissue becomes during heating. This difficulty arises in part due to blood flow and other physiological variables which modulate tissue cooling in unknown ways. Inserted temperature probes only measure temperature at one point. By measuring the spectrum of the nanoparticle magnetization, the temperature of the nanoparticles can be evaluated in real time. Using the imaging arrangement of FIG. 10, in which the sensed temperature is coupled with an image of nanoparticle location, the resulting display image of the nanoparticles provides a visible a temperature map. Such a map can be displayed in grayscale or color in which differing colors and/or intensities represent differing temperature values within a desired range, and at predetermined locations.

Other factors such as the binding energies of the nanoparticles may complicate the overall reading of nanoparticles. However the above-described measurements may be adapted to compensate for secondary factors, thereby also providing estimates for those secondary factors. For example, it is contemplated that the principles described herein can be adapted to estimate the strength of the bonds of the antibody tag. Or the principles may be adapted to estimate the phase of the substrate in which the nanoparticles are imbedded/infused. Alternative, these principles may be adapted to estimate the mechanical rigidity of the cell or extracellular matrix to which a nanoparticle is attached. In general each of the above conditions would tend to modulate the motion of the nanoparticle at a given temperature, and thus would be reflected in $H_{TE}$. By empirical and experimental techniques, the effects of these factors can be plotted and coefficients (or curves, etc.) to characterize and/or detect these factors can be determined.

Measurements of the signal at different static bias fields, or with different amplitudes of the driving field, and/or with different combinations of frequencies of driving field all can be employed to provide information about the ability of the nanoparticles to tumble or reverse magnetic polarization. This information can be used to estimate various physical properties for the nanoparticle environment.

In a further illustrative embodiment of a cancer-treatment procedure, particles with antibodies targeted for cancer cells are injected in the subject. Following binding, a very large applied magnetic field is used to heat the particles in the cancer. The ratio of the harmonics would be used to monitor heating to make sure therapeutic temperatures are achieved in the cancer. In another embodiment, the distribution of the applied fields is changes using temperature information to achieve better therapy. In another embodiment, the harmonics at a constant temperature are used to measure the binding strength of the antibody targeting agents for diagnostic or other purposes including the suitability of therapy. In another embodiment, the harmonics at a constant temperature are used to estimate the number of antibody targeted particles that are bound and the number that are unbound for diagnostic purposes or to know when to start therapy. In another embodiment, the harmonics are used to estimate when a phase change has occurred in the material in which the articles are located.

Figure 16:
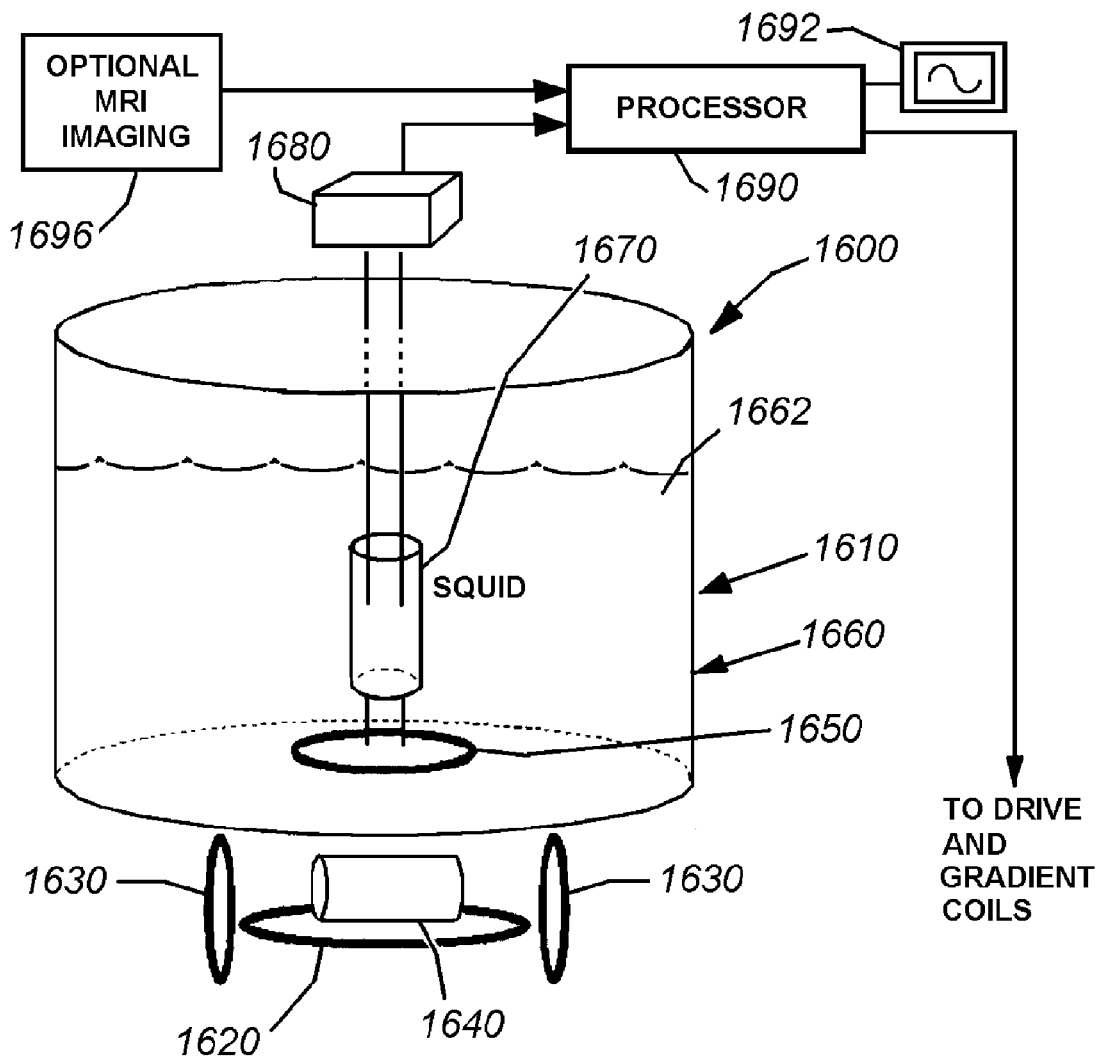
FIG. 16 is a magnetic nanoparticle detection/imaging system employing a very-high-sensitivity pickup device to measure the output signal from the magnetic nanoparticles in accordance with an illustrative embodiment.

Reference is now made to FIG. 16 which details an illustrative embodiment of an improvement to MPI device implementations, including the above-described sensing and localization embodiments, which significantly increases their sensitivity and imaging accuracy. This arrangement 1600. By way of background, MPI typically imposes a pure sinusoidal magnetic field on the sample of embedded nanoparticles. Because no hysteresis curve is perfectly linear, the magnetization of the magnetic nanoparticles is distorted slightly, which produces harmonics in the induced magnetization. The induced magnetization produces a signal in the pickup coils, and that signal exhibits energy at the harmonics of the drive frequency. Those harmonics are unique to the nanoparticles and can be separated from the signal induced by the drive field because they are at different frequencies. Currently, the nanoparticle output signal is measured in a somewhat conventional pickup coil as described generally above. The exemplary embodiment of an MPI system 1600, instead, employs a DC current or radio-frequency Superconducting Quantum Interference Device (SQUID) to increase the sensitivity of nanoparticle signal reception. The function of a SQUID, and its operation, is described in *The SQUID Handbook*, edited by John Clarke and Alex I. Braginski, Wiley-VCH, Weinheim, 2004, which is incorporated herein by reference as further background information. By using a SQUID the various harmonics in the above-described temperature sensing embodiment are better resolved, particularly for higher-order harmonics with correspondingly low signal outputs. In particular, conventional SQUID designs are capable of sensitivities on the order of $10^{-15}$ Tesla which is many orders of magnitude below that of a coil coupled to a traditional amplifier.

Further reference is now made to the exemplary MPI system 1600 of FIG. 16 MPI system which uses a SQUID detector assembly 1610 as a pickup device. Note that the illustrative drive coil 1620 and imaging gradient coils 1630 are similar, or identical to, those in previously described embodiments and/or the prior art. These coils 1620, 1630 surround a subject or sample 1640 infused with nanoparticles. The pickup coil 1650 resides over the sample 1640 and coils 1620, 1630, and is immersed in an insulated container (a cryostat) 1660 containing liquid helium 1662 to induce superconductivity (or the coil is otherwise held at a very low temperature using, for example cryogenic cooling jackets, etc.). The SQUID device 1670 is interconnected to the coil 1650 and is also immersed in the helium, or another low-temperature fluid 1662 to be maintained at a very low temperature. The system's sensing electronics 1680 interconnect to the SQUID and are located outside, adjacent to the cryostat 1660. The sensing electronics are part of, or interconnected to a data processor or other controller 1690 that also interconnects to the drive and gradient coils 1620, 1630 as shown. A display and interface 1692 provides image information and other data related to the sample 1640. The extremely high sensitivity of the SQUID device 1670 enables a very accurate image, and/or temperature (or other data) reading with respect to the sample 1640.

For optimal performance using the SQUID 1670 as a pickup device, the drive frequency generated by the drive coil 1620 should be prevented from dominating the output signal of the nanoparticles at higher harmonics. This can be accomplished in several ways. For example, the drive coil 1620 can be made resonant to the desired frequency, or a balancing coil can be placed at a location wherein it picks up the drive field but not the field output from the sample by the nanoparticles. Alternatively, the detector can be placed beside the drive coils with magnetic shielding between so the detector only observes the sample, and not the drive coil itself.

It is expressly contemplated that the SQUID device shown and described herein can be substituted for another form of "very-high-sensitivity pickup device" which can be employed in an illustrative imaging/sensing system in a generally similar position and manner. Thus, as used herein, that term should include other similar high-sensitivity devices, such as the recently developed Spin Exchange Relaxation-Free (SERF) magnetometer. A description of such a device can be found, by way of background, online in connection with the Princeton University Physics Department at the World Wide Web address: http://physics.princeton.edu/atomic/romalis/magnetometer/, the teachings of which are incorporated herein by reference by way of background.

It is also expressly contemplated that, according to this invention, a very-high-sensitivity pickup device can be applied as a detection system for any acceptable imaging system or method, or even to a system that is designed primarily to quantify the number of nanoparticles in a sample, without imaging the sample. Likewise, the SQUID or other high-sensitivity pickup can be incorporated into the imaging sensors described with reference to the above-described localization and imaging embodiments.

In accordance with this invention, the use of high-sensitivity pickups allows a variety of further subject characteristics to be measured. These characteristics include, but are not limited to, binding energies, bound fraction of nanoparticles, binding kinetics, phase changes in the materials containing the nanoparticles, and/or the stiffness of the elements the nanoparticles are bound to—such as extra-cellular matrix or cellular structures.

It is also contemplated generally that the MRI described above can be employed with any of the embodiments herein to measure particular characteristics, including binding and temperature, of particles. This is performed in the fringe field of the MRI, allowing the anatomical images produced by MRI to be co-registered with the particle images and measurements obtained using MPI techniques. The coregistration process can be accomplished using conventional image-handling techniques. As shown by way of example, in FIG. 10, the various localization and imaging embodiments can include such optional MRI imaging 1070, which is combined by the control and/or imaging components and software 1050 to produce a combined/coregistered image on the display 1060. Likewise, various temperature and other particle-characteristic sense embodiments can be combined with MRI imaging as depicted by way of example in FIG. 16. As shown the optional MRI imaging has acquired anatomical (or other) images of the subject 1640, which are then combined/coregistered with particle imaging using the controller components and software 1690 to generate the combined image on the display 1692.

The foregoing has been a detailed description of illustrative embodiments of the invention. Various modifications and additions can be made without departing from the spirit and scope of this invention. Each of the various embodiments described above may be combined with other described embodiments in order to provide multiple features. Furthermore, while the foregoing describes a number of separate embodiments of the apparatus and method of the present invention, what has been described herein is merely illustrative of the application of the principles of the present invention. In particular, it is contemplated that in most embodiments coils are arranged to generate fields that act in three dimensions, although one dimension of action may be shown for simplicity. The selection and arrangement of magnetic coils (or other selectively driven magnetic structures) should be apparent to those of ordinary skill. Moreover, the magnetic fields-as-functions-of-time employed herein can include, but are not limited, to linear and nonlinear magnetic field gradients, harmonic fields with different frequencies, different phases and different field orientations and fields that are arbitrary functions of time. The magnetic fields can vary with position with equal generality. All of the above-described embodiments can be employed as discrete systems and methods or combined with MPI methods or the imaging methods described here or other imaging methods to create images of the parameters measured. For example, by combining a plurality of systems and methods temperature maps or temperature images can be obtained instead of determining the average temperature in a single volume. In addition, while control systems are shown schematically, it should be apparent to those of ordinary skill that any acceptable arrangement of analog and/or digital electronic hardware, software (consisting of computer readable program instructions in association with a processor) or a combination of hardware and software can be employed to achieve the desired control, localization and other desired sensing and display functions. Also, while the exemplary experimental arrangement shown and described herein for the sensing of temperature is adapted for use on small samples, the scale of the arrangement can be altered in accordance with well-known design techniques to accommodate larger samples and subjects including human bodies. Likewise, a variety of additional scanning and measurement devices can be employed in accordance with ordinary skill to provide additional useful metrology. Accordingly, this description is meant to be taken only by way of example, and not to otherwise limit the scope of this invention.

What is claimed is:

1. A system for detecting temperature of magnetic nanoparticles within the interior of a subject comprising:
    a pickup device that detects output signals produced in the nanoparticles and from which the temperature is calculated;
    sensing circuitry that determines the temperature from an output of the pickup device based upon spectra of magnetization of the nanoparticles using a predetermined model for the magnetization and a plurality of harmonics of the output signal; and
    a display operatively connected to the sensing circuit that displays information related to the temperature determined by the sensing circuitry.

2. The system as set forth in claim 1 wherein the predetermined model is a Langevin function.

3. The system as set forth in claim 2 further comprising an imaging coil assembly operatively connected with the sensing circuitry so as to generate images of the nanoparticles with respect to the temperature.

4. The system as set forth in claim 3 wherein the pickup device comprises a very-high-sensitivity pickup device.

5. The system as set forth in claim 4 wherein the very-high-sensitivity pickup device comprises one of a SQUID or a SERF magnetometer.

6. The system as set forth in claim 3 further comprising an MRI constructed and arranged to derive an anatomical MRI image of the subject and wherein images of the nanoparticles are coregistered with the anatomical MRI image.

7. The system as set forth in claim 1 wherein the predetermined model is a model for hysteresis curve exhibited by the nanoparticles when magnetically excited due to thermal activity of the nanoparticles.

8. A method for detecting temperature of magnetic nanoparticles within the interior of a subject comprising:
    elevating the temperature of the nanoparticles within the interior of the subject to heat the nanoparticles;
    detecting, using a pickup device output signals produced in the nanoparticles as a result of the elevating the temperature;
    determining the temperature, using sensing circuitry, based upon the detecting using a predetermined model for magnetization and a plurality of harmonics of the output signals; and
    displaying information related to the temperature on a display operatively connected to the sensing circuitry.

9. A system of detecting temperature of magnetic nanoparticles within the interior of a subject comprising;
    a driver that induces detectable output signals in the nanoparticles within the interior of the subject;
    a very-high-sensitivity pickup device that detects the output signals;
    a sensing circuit and display assembly, operatively connected to the very-high-sensitivity pickup device that, respectively, determines the temperature based upon a spectra of magnetization of the nanoparticles using a predetermined model of the magnetization and a plurality of harmonics of the output signals; and a display operatively connected to the sensing circuit that displays information related to the temperature.

10. The system as set forth in claim 9 further comprising magnetic particle imaging coils and interconnected magnetic nanoparticle imaging circuitry, and wherein the sensing circuitry is operatively connected with the magnetic nanoparticle imaging circuitry and wherein the display is constructed an arranged to provide images of the nanoparticles.

11. The system as set forth in claim 10 further comprising an MRI constructed and arranged to derive an anatomical MRI image of the subject and wherein images of the nanoparticles are coregistered with the anatomical MRI image.

12. The system as set forth in claim 9 wherein the very-high-sensitivity pickup device comprises a SQUID.

13. The system as set forth in claim 9 wherein the very-high-sensitivity pickup device comprises a SERF magnetometer.

* * * * *